US006926732B2

(12) United States Patent
Derus et al.

(10) Patent No.: US 6,926,732 B2
(45) Date of Patent: Aug. 9, 2005

(54) STENT DELIVERY DEVICE AND METHOD

(75) Inventors: Patricia M. Derus, Rogers, MN (US); Stephen L. Bolea, Watertown, MN (US); John W. Westrum, Jr., Prior Lake, MN (US)

(73) Assignee: AMS Research Corporation, Minnetonka, MN (US)

( * ) Notice: Subject to any disclaimer, the term of this patent is extended or adjusted under 35 U.S.C. 154(b) by 13 days.

(21) Appl. No.: 09/962,402

(22) Filed: Sep. 25, 2001

(65) Prior Publication Data

US 2002/0183827 A1 Dec. 5, 2002

Related U.S. Application Data

(60) Provisional application No. 60/295,327, filed on Jun. 1, 2001, and provisional application No. 60/304,592, filed on Jul. 9, 2001.

(51) Int. Cl.$^7$ .................................................. A61F 2/06
(52) U.S. Cl. ..................................... 623/1.12; 623/1.11
(58) Field of Search ................................. 606/191, 192, 606/194, 195, 198, 200; 623/1.11, 1.12, 1.23

(56) References Cited

U.S. PATENT DOCUMENTS

| | | |
|---|---|---|
| 4,553,545 A | 11/1985 | Maass et al. |
| 4,649,922 A | 3/1987 | Wiktor |
| 4,655,771 A | 4/1987 | Wallsten |
| 4,762,128 A | 8/1988 | Rosenbluth |
| 4,771,773 A | 9/1988 | Kropf |
| 4,800,882 A | 1/1989 | Gianturco |
| 4,893,623 A | 1/1990 | Rosenbluth |
| 4,954,126 A | 9/1990 | Wallsten et al. |
| 4,990,151 A | 2/1991 | Wallsten |
| 5,026,377 A | 6/1991 | Burton et al. |
| 5,061,275 A | 10/1991 | Wallsten et al. |
| 5,078,720 A | 1/1992 | Burton et al. |
| 5,100,429 A | 3/1992 | Sinofsky et al. |
| 5,192,297 A | 3/1993 | Hull |
| 5,261,916 A | 11/1993 | Engelson |
| 5,330,482 A | 7/1994 | Gibbs et al. |
| 5,350,397 A | 9/1994 | Palermo et al. |

(Continued)

FOREIGN PATENT DOCUMENTS

| | | |
|---|---|---|
| EP | 829242 A1 | 5/1987 |
| GB | 2177927 | 2/1987 |
| WO | 92/11824 | 7/1992 |
| WO | 93/11719 | 6/1993 |
| WO | 94/20044 | 9/1994 |
| WO | 94/26174 | 11/1994 |
| WO | 95/29646 | 11/1995 |
| WO | 96/26682 | 9/1996 |
| WO | 99/55245 | 11/1999 |
| WO | 99/58083 | 11/1999 |
| WO | 00/00105 | 1/2000 |

Primary Examiner—Julian W. Woo
Assistant Examiner—Jessica R. Baxter
(74) Attorney, Agent, or Firm—Kagan Binder, PLLC

(57) ABSTRACT

A stent delivery system and method for intraluminal delivery and deployment of a self-expanding prosthesis at a site within a body canal is provided. The delivery system comprises a housing removably attached to a delivery tool. The housing stores the self-expanding prosthesis in an expanded state. The delivery tool has a catheter assembly with a capture zone. The capture zone receives and contains the self-expanding prosthesis in a compressed state. A securing mechanism couples the catheter assembly to the self-expanding prosthesis, wherein the securing mechanism transfers the self-expanding prosthesis from the housing to the capture zone immediately prior to the delivery and deployment procedure.

43 Claims, 22 Drawing Sheets

U.S. PATENT DOCUMENTS

| | | | | | |
|---|---|---|---|---|---|
| 5,356,423 A | | 10/1994 | Tihon et al. | | |
| 5,372,600 A | | 12/1994 | Beyar et al. | | |
| 5,411,507 A | | 5/1995 | Heckele | | |
| 5,464,408 A | | 11/1995 | Duc | | |
| 5,474,563 A | | 12/1995 | Myler et al. | | |
| 5,476,505 A | | 12/1995 | Limon | | |
| 5,480,423 A | * | 1/1996 | Ravenscroft et al. | ...... | 623/1.11 |
| 5,591,172 A | | 1/1997 | Bachmann et al. | | |
| 5,624,450 A | | 4/1997 | Glastra | | |
| 5,643,309 A | | 7/1997 | Myler et al. | | |
| 5,643,339 A | * | 7/1997 | Kavteladze et al. | ....... | 623/1.22 |
| 5,667,486 A | | 9/1997 | Mikulich et al. | | |
| 5,683,451 A | * | 11/1997 | Lenker et al. | ............. | 623/1.11 |
| 5,700,269 A | | 12/1997 | Pinchuk et al. | | |
| 5,702,419 A | | 12/1997 | Berry et al. | | |
| 5,713,948 A | | 2/1998 | Uflacker | | |
| 5,733,302 A | | 3/1998 | Myler et al. | | |
| 5,749,921 A | | 5/1998 | Lenker et al. | | |
| 5,759,186 A | | 6/1998 | Bachmann et al. | | |
| 5,776,186 A | | 7/1998 | Uflacker | | |
| 5,782,838 A | | 7/1998 | Beyar et al. | | |
| 5,797,952 A | | 8/1998 | Klein | | |
| 5,800,517 A | * | 9/1998 | Anderson et al. | .......... | 623/1.11 |
| 5,810,873 A | | 9/1998 | Morales | | |
| 5,814,062 A | | 9/1998 | Sepetka et al. | | |
| 5,824,041 A | * | 10/1998 | Lenker et al. | ............... | 606/195 |
| 5,843,117 A | | 12/1998 | Alt et al. | | |
| 5,843,167 A | * | 12/1998 | Dwyer et al. | ............... | 623/1.14 |
| 5,891,193 A | * | 4/1999 | Robinson et al. | ............ | 128/898 |
| 5,911,752 A | | 6/1999 | Dustrude et al. | | |
| 5,941,895 A | | 8/1999 | Myler et al. | | |
| 5,954,729 A | | 9/1999 | Bachmann et al. | | |
| 5,964,771 A | | 10/1999 | Beyar et al. | | |
| 5,976,179 A | | 11/1999 | Inoue | | |
| 5,984,957 A | | 11/1999 | Laptewicz, Jr. et al. | | |
| 6,019,779 A | | 2/2000 | Thorud et al. | | |
| 6,096,027 A | * | 8/2000 | Layne | ........................ | 606/198 |
| 6,126,685 A | * | 10/2000 | Lenker et al. | ............. | 623/1.11 |
| 6,132,458 A | | 10/2000 | Staehle et al. | | |
| 6,143,021 A | | 11/2000 | Staehle et al. | | |
| 6,149,680 A | | 11/2000 | Shelso et al. | | |
| 6,183,504 B1 | | 2/2001 | Inoue | | |
| 6,187,016 B1 | * | 2/2001 | Hedges et al. | ............... | 606/194 |
| 6,235,054 B1 | | 5/2001 | Berg et al. | | |
| 6,245,103 B1 | | 6/2001 | Stinson | | |
| 6,306,163 B1 | * | 10/2001 | Fitz | ........................... | 623/1.12 |

\* cited by examiner

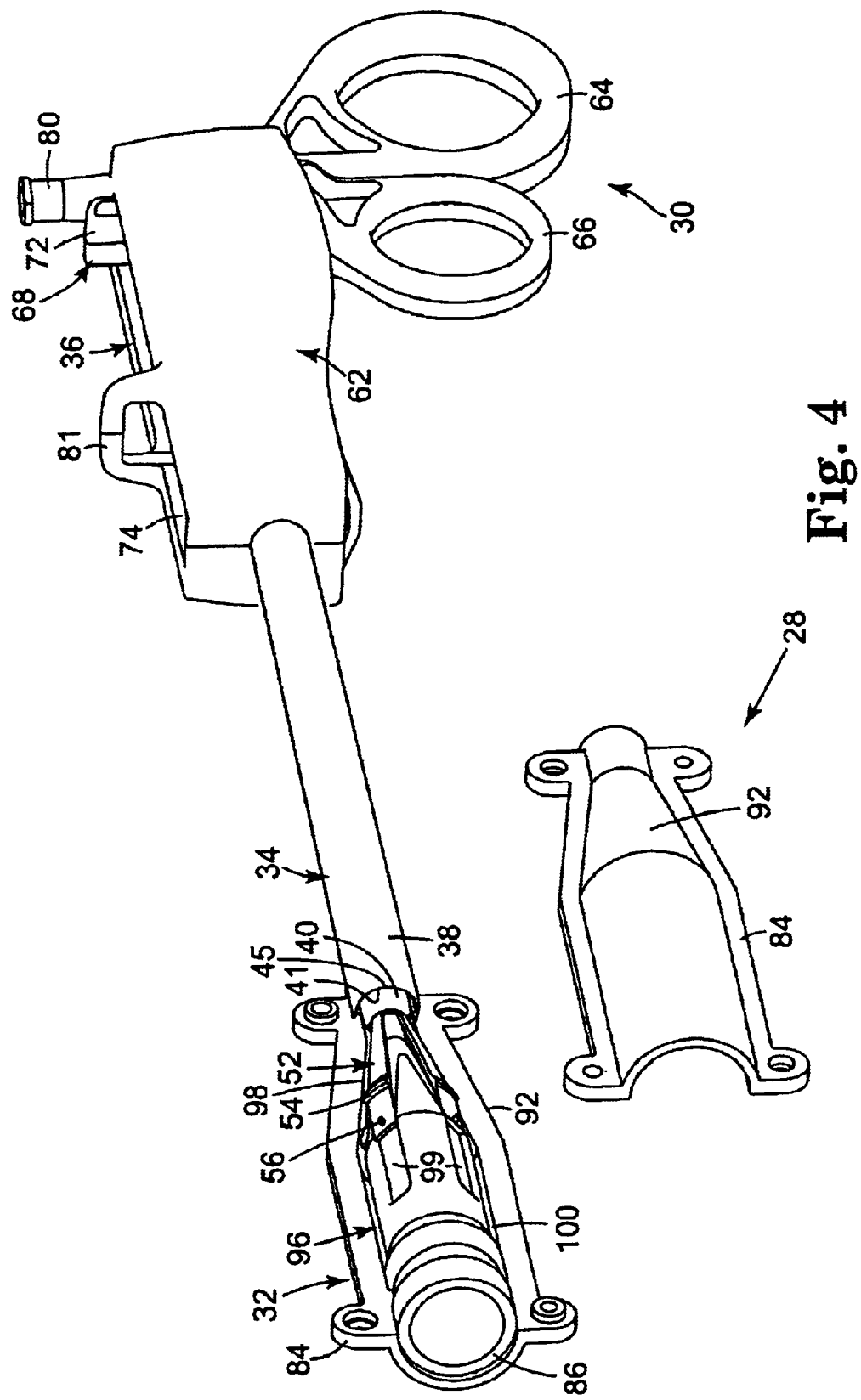

STENT DELIVERY DEVICE AND METHOD

This application claims priority to U.S. Provisional Application Ser. No. 60/295,327, filed Jun. 1, 2001; and U.S. Provisional Application Ser. No. 60/304,592, filed Jul. 9, 2001.

FIELD OF THE INVENTION

This invention relates to a stent delivery device capable of storing a self-expanding stent in an expanded state until ready for placement, at which point the stent is compressed and transferred into a delivery tool.

BACKGROUND OF THE INVENTION

Self-expanding medical prostheses, frequently referred to as stents, are well known and commercially available. They are, for example, disclosed generally in U.S. Pat. No. 4,655,771 (Wallsten), U.S. Pat. No. 5,061,275 (Wallsten et al.), and U.S. Pat. No. 5,645,559 (Hachtmann et al.). Stents are used within human body vessels for a variety of medical applications. Examples of such applications include treating stenoses, maintaining fluid openings in the urinary, biliary, tracheobronchial, esophageal, renal tracts, and vena cava filters.

It is preferable to minimize acute and chronic trauma to the luminal wall when implanting an intraluminal stent. A stent that applies a gentle radial force against the wall, and that is compliant and flexible when subjected to lumen movements, is preferred for use in diseased, weakened, or brittle lumens. Preferably, a stent is further capable of withstanding radially occlusive pressure from tumors, plaque, tissue hypertrophy and luminal recoil and remodeling.

A delivery tool that retains the stent in its radially compressed state is often used to present the stent to a treatment site within the body through tracts, lumens or vessels. The flexible nature and reduced radius of the radially compressed stent enables delivery to the treatment site through relatively small and curved tracts, lumens or vessels. In percutaneous transluminal angioplasty, an implantable endoprosthesis is introduced through a small percutaneous puncture site, airway, or port and is passed through such body vessels to the treatment site. After the stent is positioned at the treatment site, the delivery tool is actuated to release the positioned stent. The stent is allowed to self-expand within the body vessel. The delivery tool is then removed from the patient, and the stent remains in the vessel at the treated site as an implant. Typically, the delivery tool is designed for single use and is discarded.

Stents can be loosely grouped into three categories: metal, radially expanding polymeric, and fenestrated or laser-cut polymeric. Metal stents do not degrade in vivo and are, therefore, used when a permanent stent is desired. Polymeric stents are typically used to artificially and temporarily keep a lumen open. Most polymeric stents begin to degrade when exposed to water and are eventually excreted or sloughed off by the body. They do not require subsequent removal surgery. The expanding polymeric stents are comprised of a plurality of independent, woven fibers. Fenestrated stents are typically formed by providing a solid tube of polymeric stent material and using a laser to cut a pattern of holes through the wall of the tube in order to create a mesh appearance.

Each of the three types of stents have their own advantages and disadvantages. Metal stents do not degrade and maintain their strength indefinitely. Further, most metal stents do not experience significant "creep" or plastic deformation when stored in a compressed state over extended periods of time. However, as metal stents are permanent, removal requires an additional surgery. Polymeric stents are advantageous because they degrade, as discussed above. However, polymeric stents do experience creep and, therefore, may become useless if stored in a compressed state over time. Nonetheless, most polymeric stents are heretofore supplied pre-loaded in a stent delivery device and, therefore, must be used before creep occurs.

The two aforementioned types of polymeric stents exhibit some differences in performance and cost. Woven polymeric stents expand radially and shorten significantly when longitudinally compressed. Fenestrated polymeric stents resist radial expansion and longitudinal compression. Fenestrated stents are often extremely expensive, however. This expense is due to the intricate cutting that must be done with a laser to create the desired pattern. Not only is the cutting time-consuming, it results in a significant amount of wasted polymeric material. The polymeric material used to make stents is extremely expensive.

In addition to the problems associated with creep, described above, there is an additional problem with the present manner in which stents are packaged with a delivery device. Due to increasing health care costs, there is a growing demand for medical devices that can be sterilized and reused. However, as stated above, stent delivery instruments are supplied pre-loaded with a stent and are prepared for single use and disposal. This approach is not cost effective. Equipment and techniques for loading stents into a delivery tool have not yet been introduced that allow medical practitioners to load stents into delivery tools in a pre-operating room environment. Moreover, the appropriate and successful introduction of a sterilizable and reusable delivery tool requires an easy and effective loading device and a fool-proof method of use.

Thus, there remains a need for a stent delivery system that is capable of storing a stent in an expanded state until ready for placement, at which point the system permits the stent to be compressed and transferred into a delivery tool. There is also a need for a sterilizable and reusable stent delivery system which is easy to operate.

SUMMARY OF THE INVENTION

In accordance with the present invention, a delivery system and method for intraluminal delivery and deployment of an self-expanding prosthesis at a site within a body canal is provided. The delivery system comprises a housing removably attached to a delivery tool. The housing stores the self-expanding prosthesis in an expanded state. The delivery tool has a catheter assembly with a capture zone. The capture zone receives and contains the self-expanding prosthesis in a compressed state. A securing mechanism couples the catheter assembly to the self-expanding prosthesis, wherein the securing mechanism transfers the self-expanding prosthesis from the housing to the capture zone immediately prior to the delivery and deployment procedure. Thus, the likelihood of compression stress causing relaxation and/or creeping in the self-expanding stent is greatly reduced, if not eliminated.

The present invention also provides a method for delivering a self-expanding prosthesis within a body canal. The method generally comprises providing a delivery system having a cartridge or housing removably attached to a delivery tool. The self-expanding prosthesis is stored in an expanded state within the cartridge. The self-expanding prosthesis is transferred from the cartridge into the delivery tool, wherein the self-expanding prosthesis is collapsed from the expanded state to a compressed state during the transfer.

The transfer of the self-expanding prosthesis to the delivery tool is facilitated by moving an outer tube of the device distally relative to a concentric inner tube disposed within the lumen of the outer tube. The inner tube has at least one flexible arm extending axially outwardly, which has lugs that are lockingly secured to the self-expanding prosthesis, thereby able to pull the prosthesis such that the self-expanding prosthesis passes through the cartridge and into the lumen of the outer tube when the outer tube is moved distally relative to the inner tube. Preferably, the self-expanding prosthesis is collapsed from the expanded state to the compressed state by passing through a funnel portion of the housing.

Other objects, features, and advantages of the present invention will become apparent from consideration of the following detailed description.

BRIEF DESCRIPTION OF THE DRAWINGS

FIG. 4 is a perspective view of a delivery system of the present invention with a section of the cartridge cover removed to show the details of a preferred guide;

DETAILED DESCRIPTION OF PREFERRED EMBODIMENTS OF THE INVENTION

Figure 1:
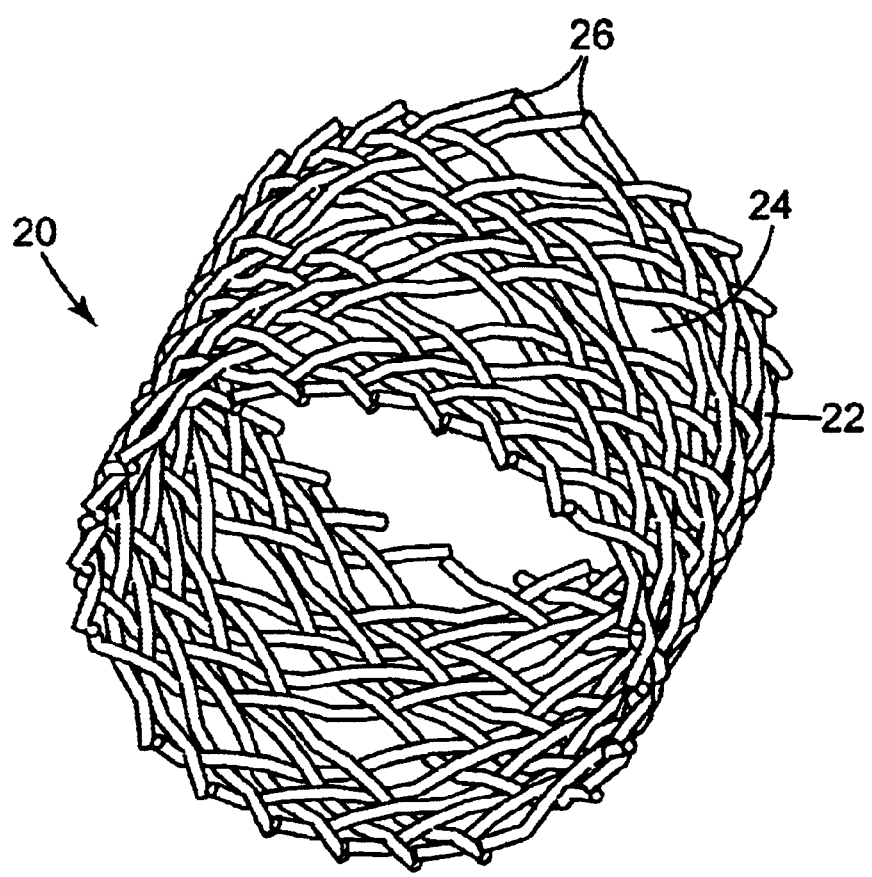
FIG. 1 is a prospective view of a stent which is exemplary of the type of self-expanding, radially compressible tubular prosthesis which may be placed using a delivery system in accordance with the present invention.

The present invention relates to a method and apparatus for intraluminal delivery and deployment of a self-expanding prosthesis at a site within a body canal. In the particular embodiments shown in the drawings and herein described, the delivery systems include a delivery tool and a stent cartridge, wherein the stent is stored in the stent cartridge in an expanded state. The stent is transferred to the delivery tool on-site and immediately prior to the delivery and deployment procedure. Among the advantages of such a delivery system is that stress relaxation and/or creep of the stent is minimized. This is particularly important for polymeric stents which may exhibit substantial stress relaxation and creep if stored in a compressed state over a long period of time. Furthermore, the likelihood of contaminating the stent during the loading procedure is reduced because the stent is enclosed in the stent cartridge before and during the loading procedure. Still further, the loading procedure is greatly simplified by providing the delivery system with a stent cartridge pre-attached to the delivery tool.

The delivery systems of the present invention are shown to deploy a self-expandable stent. However, it should be understood that the principles of the invention are equally applicable to virtually any expandable prosthesis. For example, the delivery system may be used to deliver a self-expanding or balloon expandable graft, stent-graft or the like. Therefore, the present invention should not be limited to the specific embodiments shown and such principles should be broadly construed.

Referring to FIG. 1, an exemplary prosthesis in the form of a self-expandable stent 20 is illustrated. The stent 20 comprises a plurality of interwoven or interconnected fibers or wires 22 and has a flexible tubular shape with rows of interconnected cells 24 defined by the fibers 22. The ends of the stent 20 may include loops 26 extending longitudinally outward in the distal and proximal direction. It is noted that the present invention is equally applicable for polymeric or other types of stents. The length of the stent 20 may range from about 10 mm to 500 mm, preferably from 10 mm to 50 mm, and the relaxed diameter range from about 4 mm to 45 mm, preferably being in the range from about 5 mm to 25 mm. Such stents 20 are particularly suitable for the treatment of various occlusive conditions such as atherosclerotic or arteriosclerotic iliac artery stenosis and provides mechanical support to compress intimal flaps and dissections against the vessel wall after percutaneous transluminal angioplasty. Additionally, the stent 20 mechanically supports arterial sclerotic plaque in the vessel passage, which inhibits restenosis and occlusion. The stent 20 may also be used to treat benign prostatic hyperplasia (also referred to as enlarged prostate gland), to bridge an aneurysm, or in a biliary, coronary, cerebral or any peripheral vascular site.

Referring to FIGS. 2–5, a delivery system 28 configured in accordance with the principles of the present invention is illustrated. The delivery system 28 includes a delivery tool 30 and a stent cartridge 32 for storing a self-expanding stent 20 in an expanded state. The stent cartridge 32 is attached to a distal end 45 of the delivery tool 30. The delivery tool 30 may also be used to deliver non self-expanding prostheses such as a balloon expandable stent. For example, many fenestrated stents lack the expansion force of woven stents. A balloon may be used within the stent to ensure the stent frees itself of the delivery tool and assumes a desired size.

The delivery tool 30 includes a catheter assembly 34 and a hand piece 36. The catheter assembly 34 is about 20 cm in length and includes an outer tube 38 and an inner tube 40. The outer tube 38 has a lumen 41 extending from a proximal end 43 to the distal end 45. The outer tube 38 is preferably strong enough to withstand the expansion force of the stent 20 and, in some embodiments, may also be flexible enough to allow intralumenal maneuvering. The outer tube 38 may be formed of a high strength thermoplastic elastomer such as nylon, PTFE, polyvinylcholoride, PEEK™, ULTEM™, PEBAX™, or the like. Alternatively, the outer tube 38 may be formed of a braided reinforced polymer tubing or a liner reinforced tubing, preferably having fibers of a polyamide such as VECTRAN™, KEVLAR™, SPECTRA™, or the like embedded to improve tensile strength without reducing flexibility. The outer tube 38 provides high column strength with flexibility and may be helically formed from a tightly wound, high strength material such as reinforced stainless steel wound over polyimide tubing. In applications where a flexible outer tube is not required, rigid stainless steel tubing may be used.

The inner tube 40 is slidably received within the lumen 41 of the outer tube 38 and may be formed from a polyamide such as ULTEM™, PEEK™, polyvinylchloride, nylon, PTFE, or a thermoset plastic such as polyimide. Preferably, the inner tube 40 is formed from stainless steel. The inner tube 40 includes a lumen 48 for the passage of a guide wire (not shown) or other devices. These other devices may include, but are by no means limited to, endoscopes or other viewing equipment, or balloon delivery devices to aid in expanding the stent 20, such as discussed above. The lumen 48 is aligned with a access port 104 in the hand piece 36 thereby providing a physician access to the lumen 48. Also, an opening 82 leading to the lumen 48 is formed in the proximal end of the inner tube 40 and is aligned for fluid communication with a fluid inlet port 80 defined by the body 68. The functions and details of the access port 104 and the fluid inlet port 80 are discussed below.

At the distal end 47 of the inner tube 40, a securing member 50 extends outwardly therefrom. The securing member 50 is useable to draw a stent 20 into the distal end 45 of the outer tube 38 and also to deploy the stent 20 therefrom during a stent placement operation. The physical features of the securing member 50 are now described, however, the dynamics of the member 50 are described later herein.

In the exemplary embodiment, the securing member 50 is shown as a plurality of flexible arms 52. Each of the flexible arms 52 may include pads 54 and lugs 56. Each lug 56 is constructed and arranged to engage one of the proximally located loops 26 or cells 24 of the stent 20. The pads 54 are constructed and arranged to act against the inside surface of the outer tube 38 to maintain the arms 52, and subsequently the lugs 56, in a compact configuration when the stent 20 is being deployed. As will be described below, the outer tube 38 is moveable relative to the inner tube 40 during deployment and there are a plurality of stops 70 which correspond to various relative positions between the tubes 38 and 40. One of these positions is a deployment position whereby the stent 20 is completely free of the outer tube 38 and allowed to expand but the pads 54 are still within the outer tube 38, thereby preventing the arms 52 from spreading and interfering with the deployment of the stent 20. Of course, any arrangement capable of securing the proximal area of the stent 20 to the inner tube 40 may be used. For example, the proximal area of the stent 20 may be secured with retractable pins (not shown) extending radially outwardly from the inner tube 40, wherein the stent 20 is in a secured state when the pins are extended, and the stent 20 is in an unsecured state when the pins are retracted.

To facilitate proper placement of the catheter assembly 34, one or more marker elements (not shown) may be located at a predetermined position on the outer tube 38 and/or inner tube 40, respectively. The marker elements may be a band of metal or radiopaque material attached to the periphery of the outer tube 38 and/or inner tube 40, whereby correct placement of the catheter assembly 34 prior to deployment of the stent 20 may be checked by fluoroscopy. Further, the distal end of the inner tube 40 may include a radiopaque element, thereby giving an indication of the location of the distal end of the stent 20 during fluoroscopically guided prostheses placement.

Figure 2:
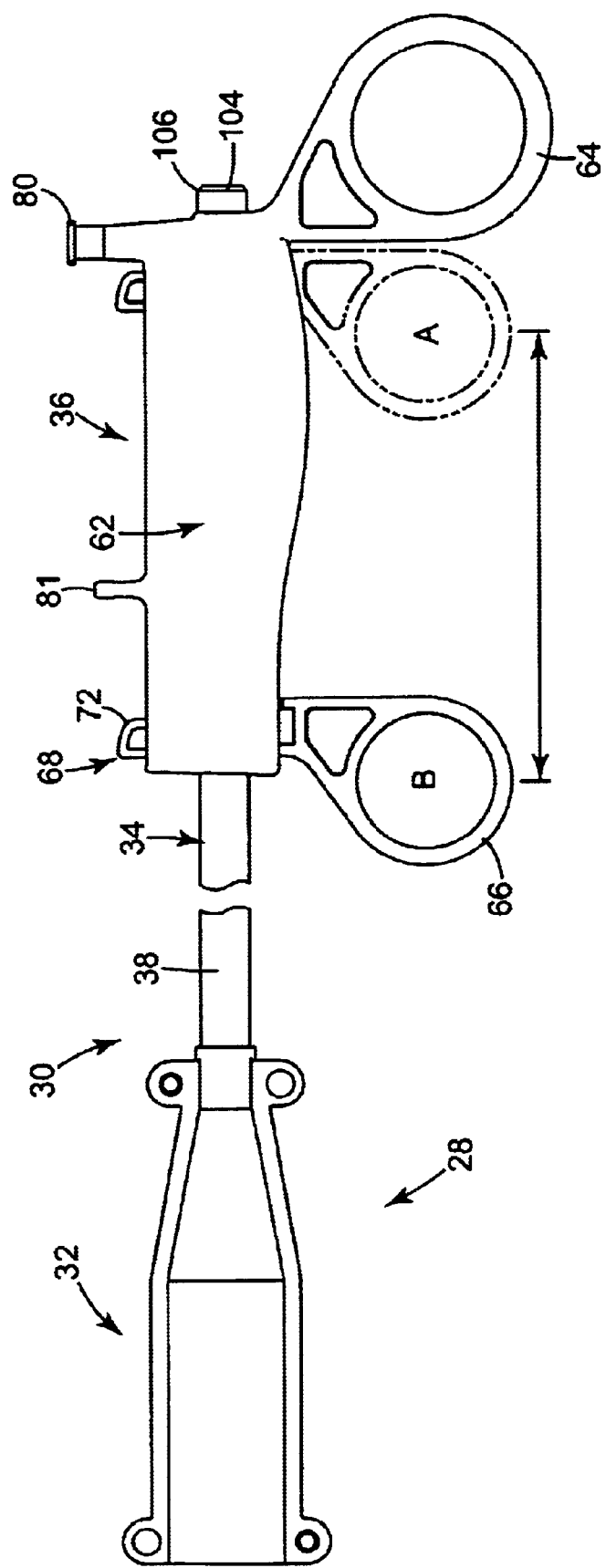
FIG. 2 is a side elevation of an exemplary delivery system in accordance with the present invention for delivering the stent of FIG. 1.
Figure 3:
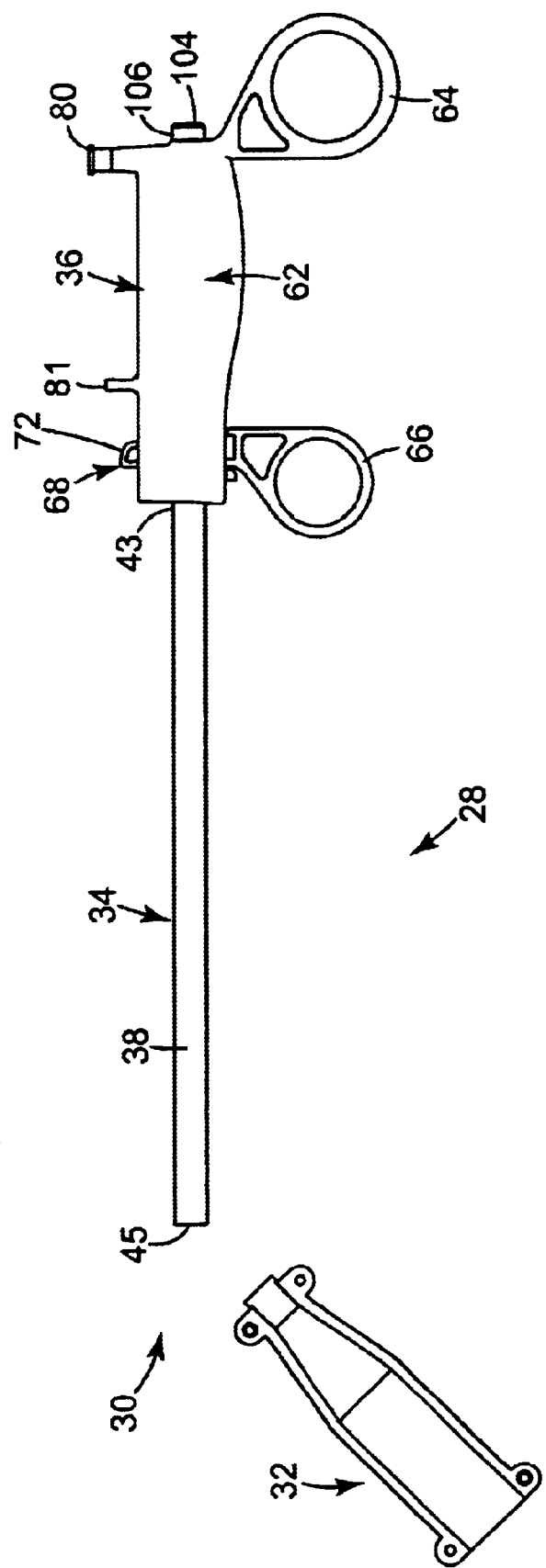
FIG. 3 is a side elevation of the delivery system of FIG. 2 with the cartridge separated from the delivery device.

The hand piece 36 is attached to the proximal ends of the outer tube 38 and the inner tube 40. The hand piece 36 includes a main body 62 and a rear loop handle 64 integral therewith. The hand piece 36 further includes a moveable forward loop handle 66 which is slidable between extreme positions within the main body 62 indicated by dashed lines and full lines in FIG. 2 illustrating a retracted position "A" and a forward position "B", respectively. The outer tube 38 is fixedly attached to the forward loop handle 66 and thus moves axially forward and backward, over the inner tube 40, when the forward loop handle 66 is moved between the "A" and "B" positions.

The hand piece 36 includes a safety catch release member 68 which is preferably integral with, and therefore moves with, the forward loop handle 66. The release member 68 is constructed and arranged to interact with a plurality of upper stops 70 located on the inside upper surface of the hand piece body 62 (FIG. 5). These stops 70 are provided at predetermined locations to prevent unintentional movement of the outer tube. The specific functions corresponding to the various locations of these stops 70 is discussed in more detail below. The release member 68 is preferably constructed to form an upwardly biased leaf spring which has a protuberance 72 that extends through a slot 74 (FIG. 4) in the top of the body 62 for access by a physician.

Figure 5A:
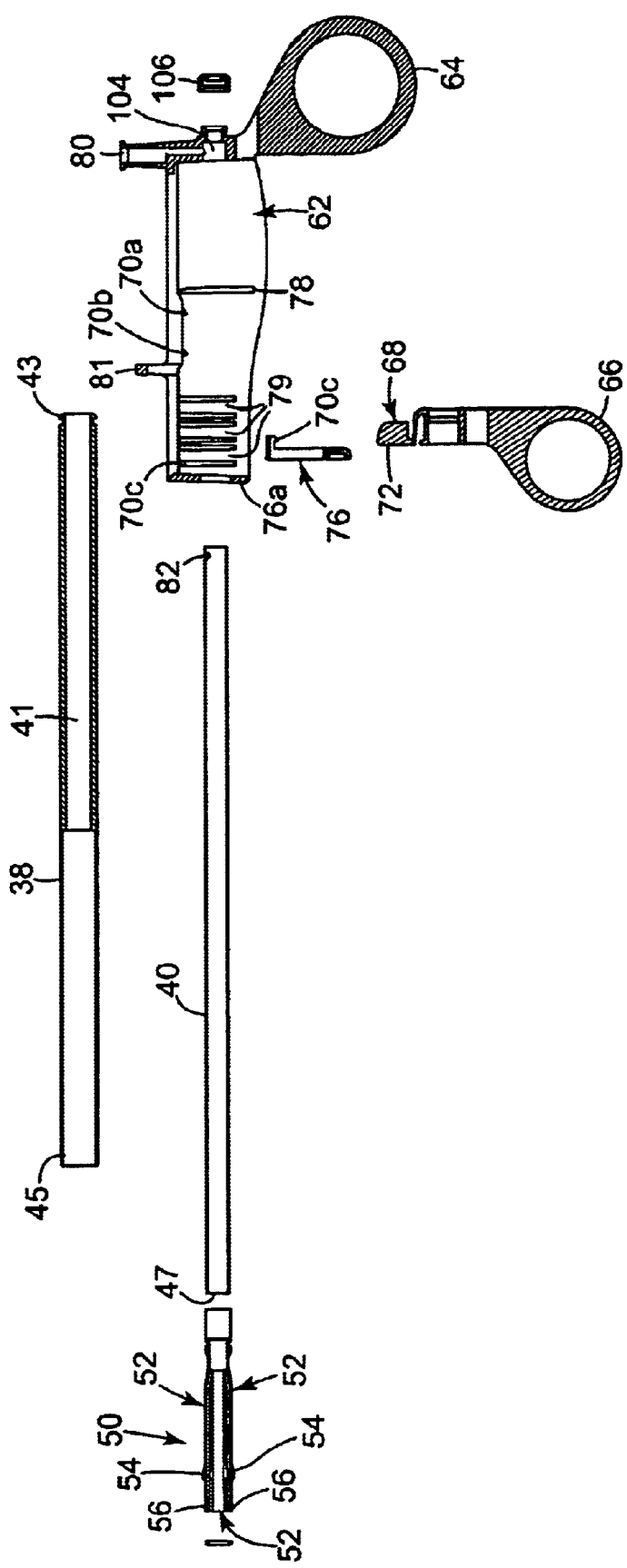
FIG. 5a is an exploded side view of a delivery tool for the delivery system of FIG. 2.
Figure 5B:
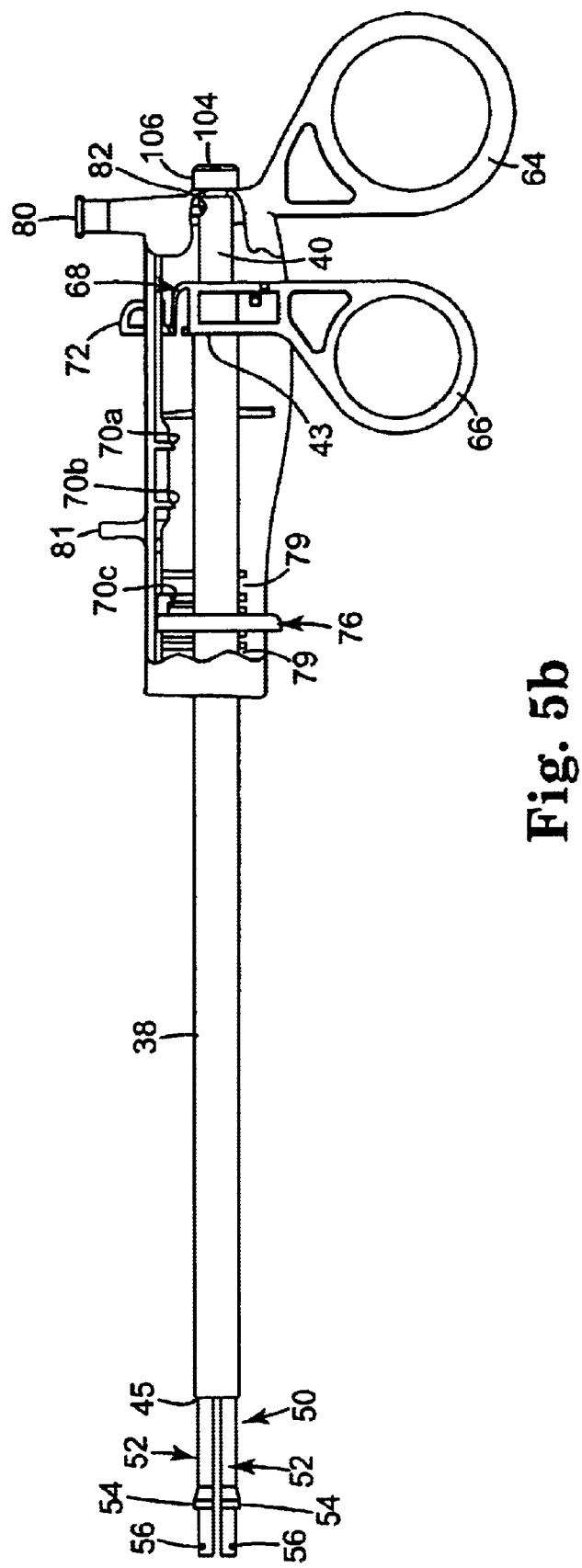
FIG. 5b is an assembled side view of the delivery tool of FIG. 5a with a side of the body cutaway.

Looking at FIGS. 5a and 5b, the specific functions corresponding to the various locations of each of the stops 70 is clarified. Beginning at the proximal end of the hand piece 36, the first stop 70 encountered by the release member 68 as the forward loop handle 66 is moved distally from position "A" is the deployment stop 70a. The deployment stop 70a acts in concert with the side catches 78 (discussed below) to prevent the outer tube 38 from moving too far proximally when the stent 20 is being deployed in vivo. If the outer tube 38 were to move too far in a proximal direction, the arms 52 would extend too far from the distal end of the outer tube 38 and would spread apart excessively, thereby creating the risk of damaging the surrounding tissue, snagging the stent 20, or both. The deployment stop 70a is angled to allow the release member 68 to pass under the stop 70a while the forward loop handle 66 is being moved toward position "B" during the loading of the stent 20.

The next stop 70 encountered by the release member 68 while the forward loop handle 66 is moved distally toward position "B" is the pre-release stop 70b. The pre-release stop 70b is also angled to allow the release member 68 to pass under the stop 70b while the forward loop handle 66 is being moved toward position "B" during the loading of the stent 20. During a stent deployment operation, the pre-release stop 70b functions to stop the proximal movement of the outer tube 38 just prior to the release of the stent 20. At this point of the deployment, most of the stent 20 is exposed and extends from the distal end of the outer tube 38. However, the arms 52 and their lugs 56 are still within the outer tube 38 and the stent 20 is, therefore, securely attached to the device tool 30. The pre-release stop 70b provides the physician a final opportunity to ensure that the stent 20 is in the proper position before release.

The most distal stop 70 is the insertion stop 70c. The insertion stop 70c, like all of the stops 70, is angled to allow the release member 68 to pass under the stop while the forward loop handle 66 is being moved toward position "B" during the loading of the stent 20. The insertion stop 70c, in fact, assists in defining position "B". The insertion stop 70c is located to correspond with an outer tube 38 position which allows enough room between the distal end of the securing member 50 and the distal end 45 of the outer tube 38 to create a capture zone 94 (discussed in more detail below) sized to accommodate a given stent 20 of a predetermined length. The insertion stop 70c engages the release member 68 when the forward loop handle achieves position "B" during a loading operation. The insertion stop 70c then retains the stent 20 within the outer tube 38 during the insertion of the delivery tool 30 into the body of the patient, en route to the target site. Thus, the insertion stop 70c prevents the individual strands 22 of the stent 20 from extending past the distal end 45 of the outer tube 38 while the tool 30 is being placed into the patient, thereby preventing the strands 22 from damaging surrounding tissue as the tool 30 passes thereby.

Further protection against unintentional movement is provided in the form of a distal wall 76 and side catches 78 formed on the inside side walls of the body 62. Distal wall 76 is preferably a removable piece which fits into a plurality of slots 79 extending inwardly from the side walls of the body 62. Distal wall 76 prevents distal movement of the forward loop handle 66 beyond the extreme position "B". The wall 76 is removable so that it may be repositioned within the slots 79 when the device 28 is used for stents of various lengths. A longer stent 20 requires that the outer tube 38 be distally moved further than a shorter stent 20 in order to completely cover the stent 20 during insertion into a patient. The distal wall 76 further includes the insertion stop 70c so the insertion stop 70c remains in an appropriate position when the distal wall 76 is moved. Notably, a second, permanent, distal wall 76a and associated insertion stop 70c also exists such that a maximum stent length setting may be achieved by removing the removable piece 76. The permanent wall 76a and associated insertion stop 70c are out of operable range when the removable wall 76 is inserted in a slot 79.

Side catches 78 oppose each other and are located between positions "A" and "B". Side catches 78 have angled proximal surfaces and normal distal surfaces, relative to the side walls of the body 62, such that the forward loop handle 66 is allowed to pass through the side catches 78 when the handle 62 is moved distally from position "A" to position "B" during stent loading. However, once the stent is loaded, it is undesirable to allow the arms 52 to extend beyond the distal end 45 of the outer tube 38 more than necessary to release a stent 20 in vivo. Therefore, the normal surfaces of the side catches 78 prevent the forward loop handle 66 from reassuming position "A". The side catches 78, not only act in concert with the stops 70 to provide a three-point barrier against unintentional movement, they are not bypassed when the release protuberance 72 is pressed. Clearly, a wide variety of mechanisms are available to move the outer tube 38 in the distal and proximal directions. It is particularly advantageous to provide a mechanism which allows manipulation with a single hand, thus allowing the alternate hand to manipulate the outer tube 38 relative to the hand piece 36.

A final protection against unintentional movement of the outer tube 38 is provided by an obstruction 81 extending upwardly from the hand piece 36 and preferably bridging the slot 74. The obstruction 81 prevents an operating physician from nonchalantly holding the safety catch release member 68 down and using it to slide the forward loop handle 66 proximally, thereby passing some or all of the stops 70. The obstruction 81 is preferably located distally adjacent to the pre-release stop 70b so the stent 20 is not deployed prematurely.

The main body 62 of the delivery device 30 defines an access port 104 leading into the inner lumen 48 of the inner tube 40, as best seen in FIGS. 5a and 5b. An end cap 106 may be provided for creating a softer border to the entrance of the access port 104, thereby making insertion of an endoscope easier and also protecting delicate lens material from inadvertent scratching. The main body 62 further includes a fluid inlet 80 at the proximal end to allow introduction of a fluid into the delivery tool 30, such as a liquid for flushing or contrast medium for X-ray inspection. Such fluid entering the fluid inlet 80 passes through the opening 82 of the inner tube 40 and through the lumen 48. The inner tube 40 is mounted to the hand piece 36 such that the opening 82 is aligned with fluid inlet 80.

Figure 6:
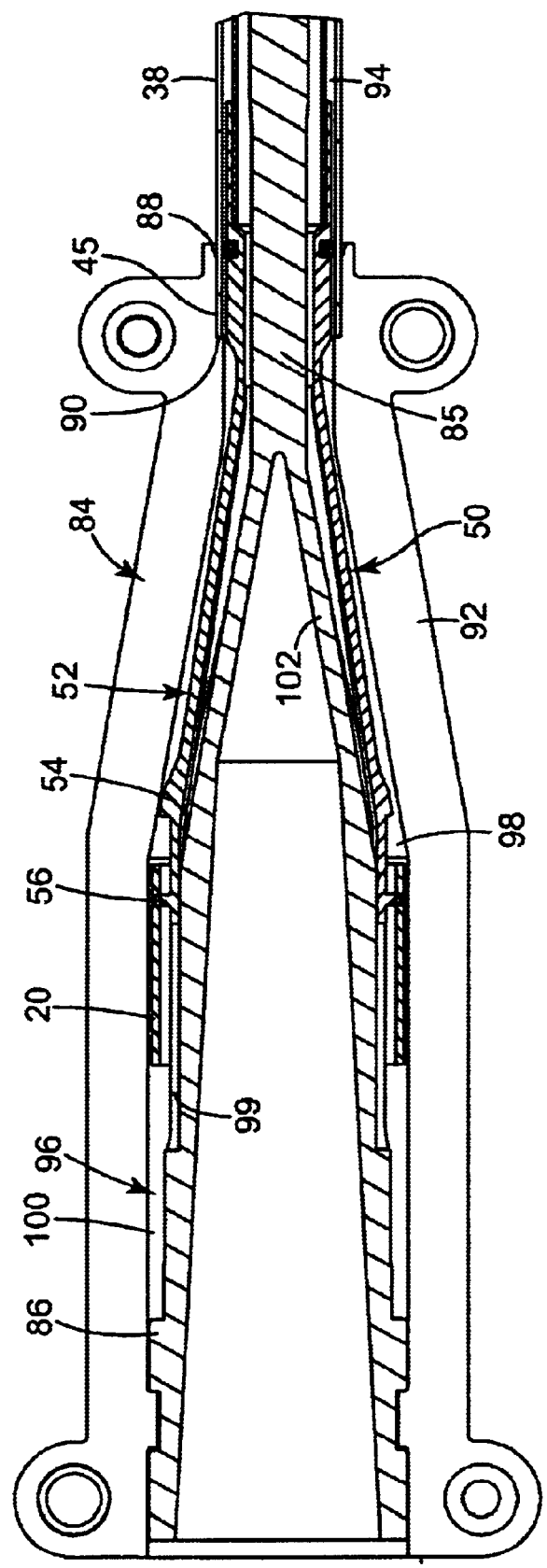
FIG. 6 is an enlarged cross-sectional view of the delivery system of FIG. 2 illustrating the stent in an expanded state and engaged with the securing member.

As described initially, the delivery system 28 includes a delivery tool or device 30 and a stent cartridge 32. Referring to FIGS. 4 and 6, the stent cartridge 32 includes a casing 84 and a stent guide 86. The casing 84 has an opening 88 at a proximal, stent delivery end and is shaped and sized for slipping over the distal end 45 of the outer tube 38. A rest 90 within the stent delivery end is located for seating the casing along an axis "A" and in position over the outer tube 38. An angled portion 92 is located between the stent delivery end and the distal end of the stent cartridge 32. The angled portion 92 is shaped for collapsing the self-expanding stent 20 before loading into stent capture zone 94 of the lumen 48 in the outer tube 38.

The stent guide 86 is located within the casing 84. The exterior surface of the stent guide 86 is shaped similarly to the interior surface of the casing 84 to form a guide space 96 having a first region 98 and a second region 100. The stent guide 86 includes a funnel portion 102 appropriately sized such that the first region 98 is slightly larger than the second region 100 to accommodate the plurality of flexible arms 52, pads 54, lugs 56, and a proximal portion of the stent 20. Preferably, the first region 98 comprises grooves 99 constructed and arranged to slidingly accept the arms 52. The grooves 99 not only provide the additional room to needed to accommodate the arms 52, pads 54 and lugs 56, they act as guides for arms 52 during loading and unloading operations. The first region 98 is further sized accordingly so that the inner face of the pad 54 slidingly contacts the outer surface of the stent guide 86 and the outer ends of the lugs 56 approach or slidingly contact the inner surface of the casing 84. The wires 22 are engaged with the lugs 56 such that the stent 20 is interposed between the outer surface of the arms 52 and the inner surface of the casing 84. Thus, the inner surface of the casing 84 prevents the stent 20 from becoming disengaged from the securing member 50.

The stent guide 86 further includes an extension 85 which extends from the proximal end of the casing 84 and into the lumen 41 of the inner tube 40. The extension 85 is preferably integral with the rest of the guide 86 and serves to prevent the stent 20 from collapsing when the stent 20 is initially compressed. Without the extension 85, there is an occasional tendency for a stent 20 to compress in such a manner that the inner lumen of the stent 20 is no longer cylindrical. This is problematic because it prevents a physician from being able to see through the inner lumen of the stent 20 to the target site when using a viewing instrument such as an endoscope. The extension 85, thus serves to initially ensure a cylindrically compressed state is achieved by the stent 20, before the guide 86 is removed.

Figure 7:
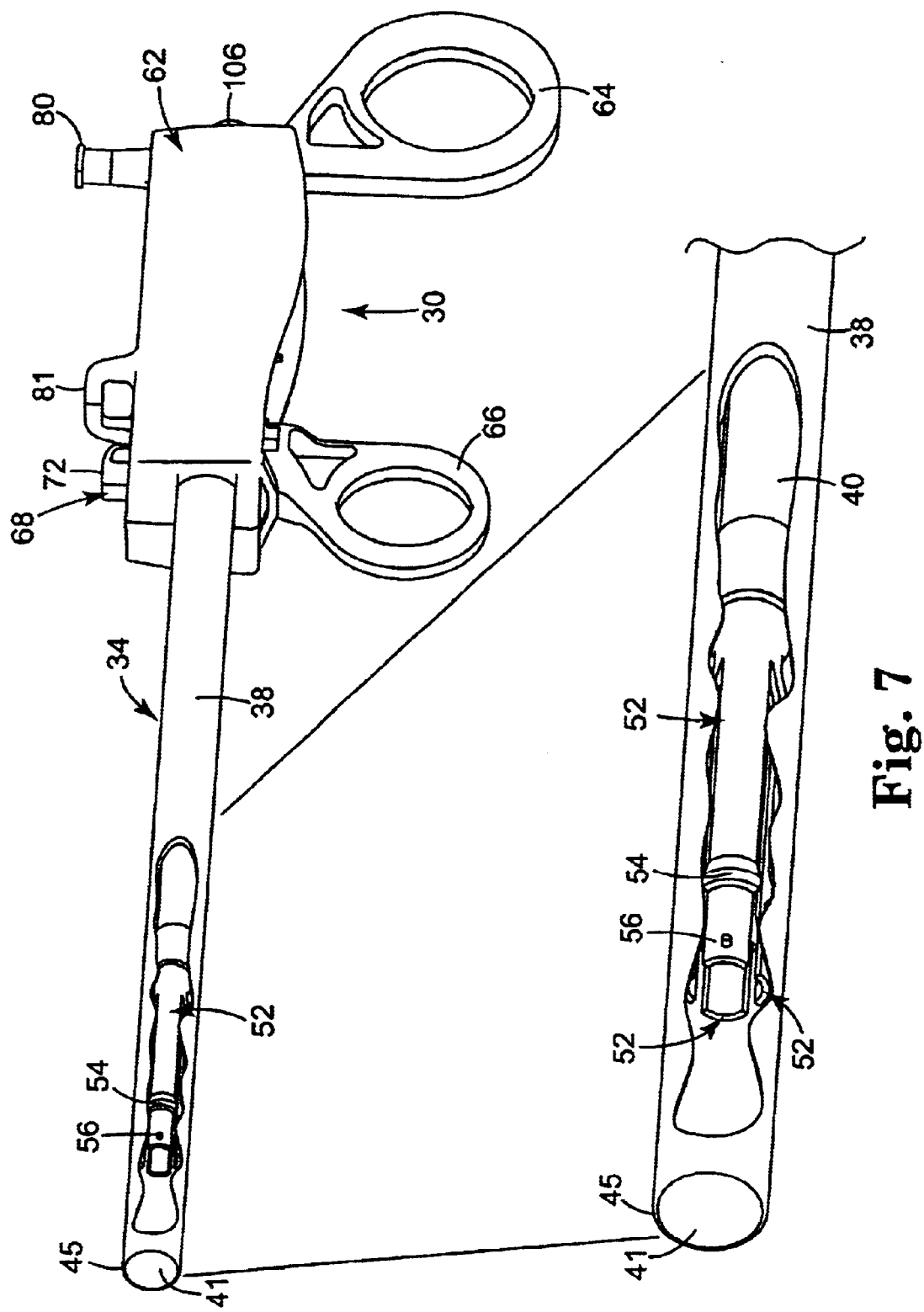
FIG. 7 is a perspective view of a preferred delivery device of the present invention with a cut-out showing the details of the securing member in an insertion position with the stent omitted to better show detail.

The extension 85 further serves to prevent a similar collapsing problem does not occur with the arms 52. As best seen in FIG. 7, the arms 52 are formed by cutting a tube into a number, preferably four, equal, longitudinal sections. These sections, thus, reform the tube shape when they are fully compressed. The extension 85 (FIG. 6) penetrates the inner lumen 41 of the inner tube 40 enough so that when the arms 52 are drawn into the inner tube 40, during a stent compression operation, they compress and reunite to form the tube shape around the extension 85. The extension 85 thus prevents one of the arms 52 from collapsing too far and disengaging from the stent 20 and/or occluding the view channel formed by the inner lumen 41.

Figure 22:
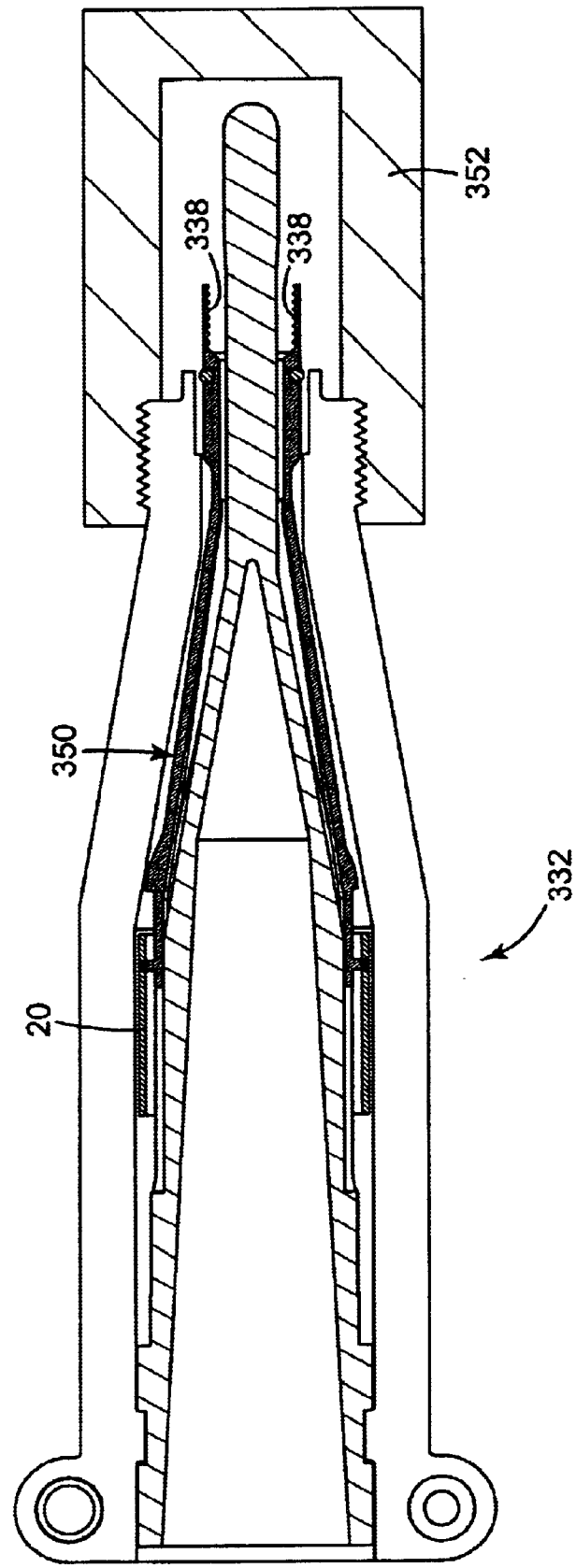
FIG. 22 is an elevational cross-section of an embodiment of a cartridge of the present invention constructed and arranged for individual packaging; and, FIG. 23 is an elevational cross-section of the cartridge of FIG. 22 attached to an alternative delivery device of the present invention.
Figure 23:
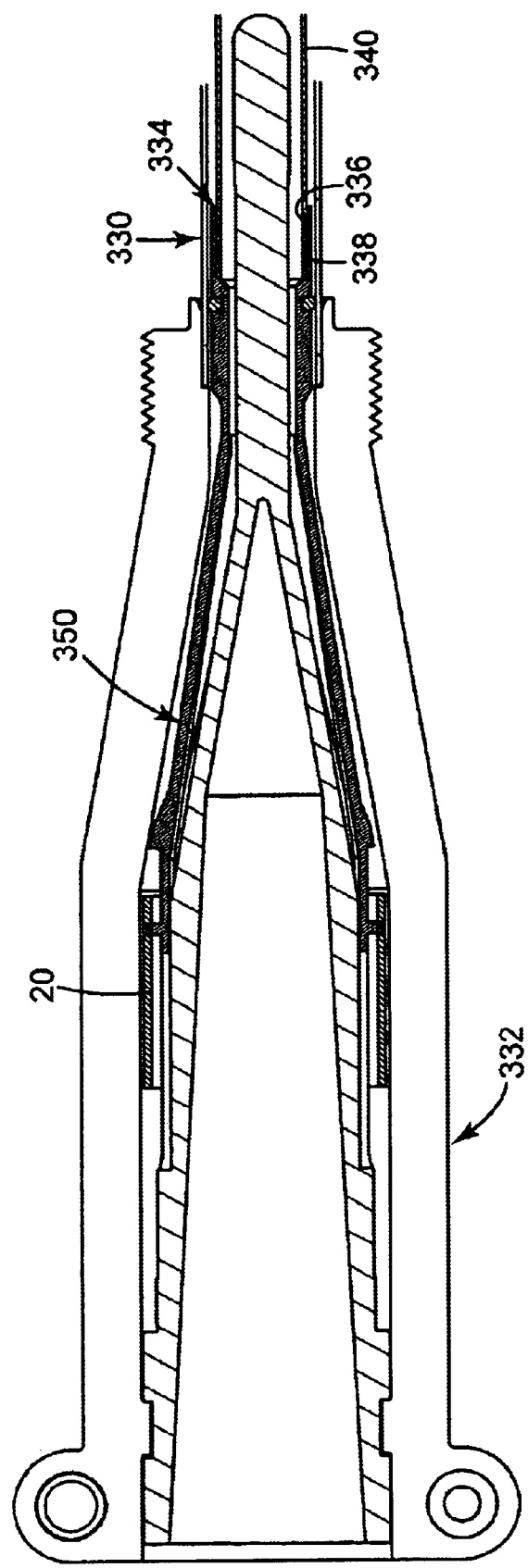

Though the stent cartridge 32 is constructed and arranged to be assembled with a stent 20 loaded thereon, and attached to and packaged with the delivery device 30, certain advantages are realized by providing a cartridge 332, such as that shown in FIGS. 22 and 23, capable of being sterilized and packaged independently from the delivery device 30. The cartridge 332 is attached to the end of a delivery device 330 by a physician prior to use. The cartridge 332 and delivery device 330 are very similar to those described above except that an attachment mechanism 334 is provided useable to join the inner tube 340 to the securing member 350. This allows the securing member 350 to be sterilized and packaged as part of the cartridge 332. A preferred embodiment is shown in FIGS. 22 and 23 whereby the attachment mechanism 334 comprises mating threads 336 and 338 formed in the distal end of the inner tube 340 and the proximal end of the securing member 350, respectively. Alternatively, various mechanisms could be utilized to accomplish the function of joining the securing member 350 to the inner tube 340. Just a few examples include snap-fit connections, bayonet connections, channel lock connections, and the like. Additionally, a cap 352 is preferably provided for maintaining a controlled, possibly pressurized, environment within the cartridge 332 during storage. For example, the cartridge 332 may be filled with nitrogen gas during storage.

Figure 8:
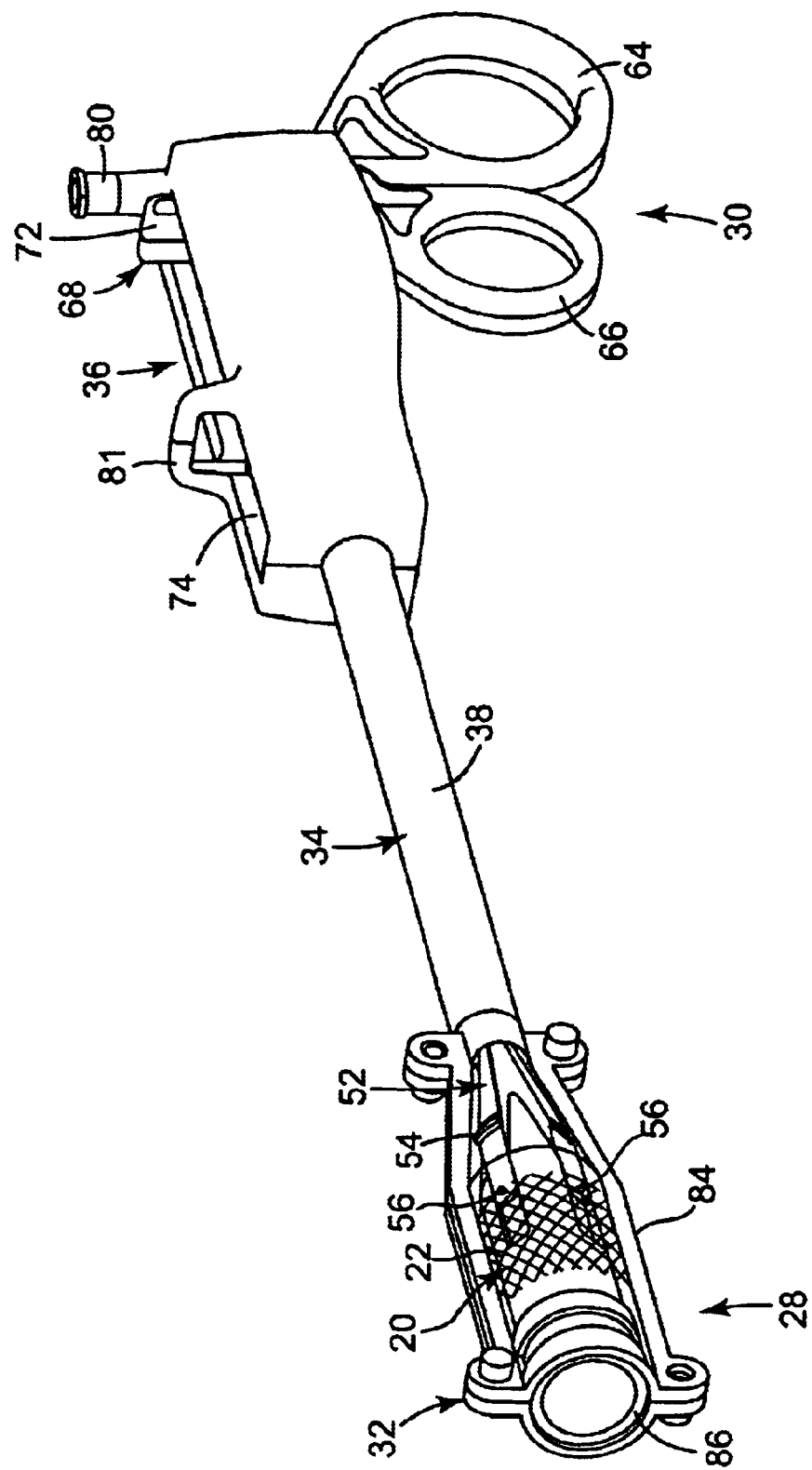
FIG. 8 is a perspective view of a preferred delivery system of the present invention with a stent loaded into the cartridge and in an expanded state prior to loading.
Figure 9:
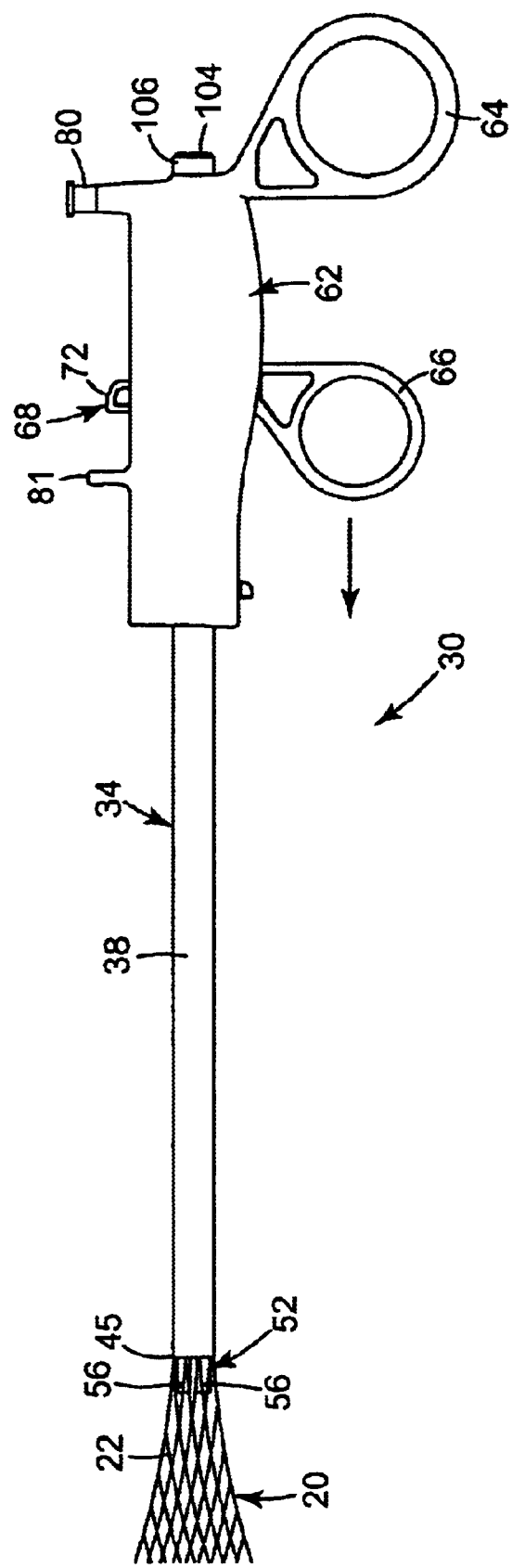
FIG. 9 is a side elevation of a stent being pulled into a preferred delivery device of the present invention omitting the cartridge to show stent detail.
Figure 10:
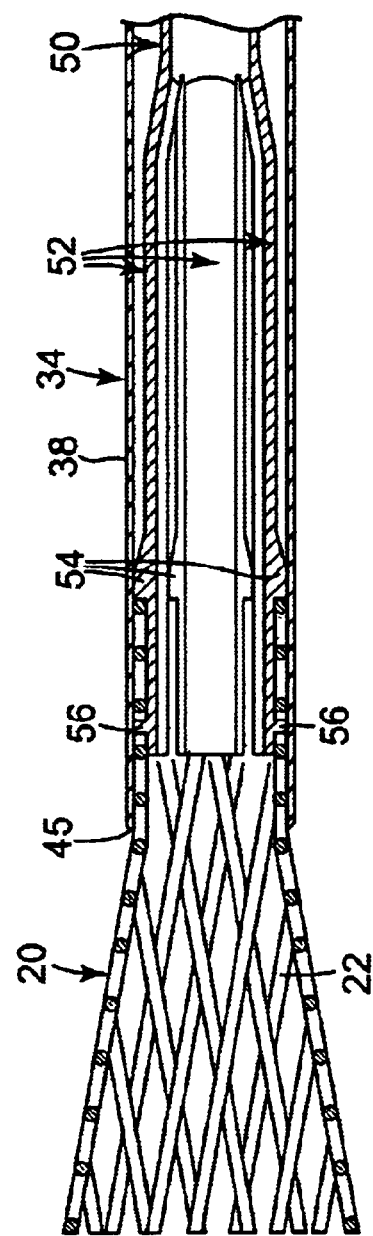
FIG. 10 is an enlarged cross-sectional elevation of a stent being pulled into the distal end of a preferred delivery device of the present invention omitting the cartridge to show the details of the interaction between the stent and the securing member.
Figure 11:
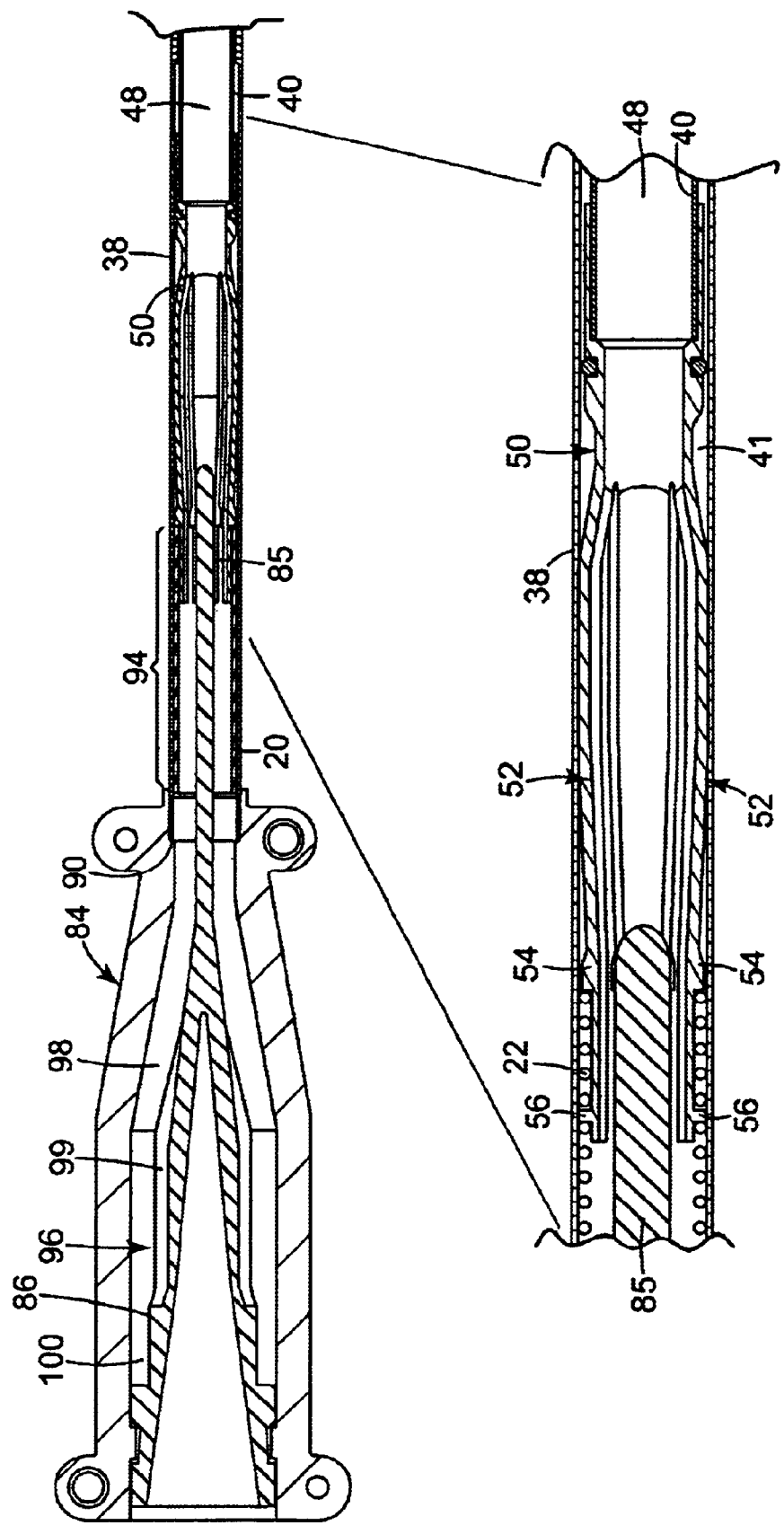
FIG. 11 is an enlarged cross-sectional elevation of a stent having been pulled into the capture zone of a preferred delivery device of the present invention with the cartridge still attached.

A full explanation of the operation of the delivery system 28 is now provided. As shown in FIG. 8, the stent cartridge 32 is initially attached to the delivery tool 30 and may be provided in a sterile package. The forward loop handle 66 is in the retracted position "A", and the lugs 56 of the securing member 50 are engaged with the wires 22 of the stent 20 to secure the stent 20 onto the inner tube 40. Immediately prior to the implantation procedure, the stent 20 is transferred from the stent cartridge 32 to the delivery tool 30 by depressing the safety catch release member 72 and moving the forward loop handle 66 from the retracted position "A" to the forward position "B" as shown in FIGS. 2 and 9–10. FIG. 2 shows position "B". FIG. 9 shows the stent 20 being drawn into the outer tube 38 as the forward loop handle 66 is moved distally as shown by the arrow. The stent 20 is shown without the cartridge 32 in FIGS. 9 and 10 for clarity. FIG. 10 shows how the securing device 50 pulls the stent 20 inside the outer tube 38. When the forward loop handle 66 is moved to the forward position "B", the outer tube 38, casing 84, and stent guide 86 move into the position shown in FIG. 11, and the safety catch release member 68 is activated to lock the forward loop handle 66 in place. During the forward movement of the forward loop handle 66, the securing member 50 and stent 20 pass through the guide space 96 and into the stent capture zone 94 of the outer tube 38. The empty cartridge 32 is detached from the tool 30 and discarded.

The tool 30 is now in the correct position to be inserted into the body until the distal end 45 is at the target site. The inner lumen 48 of the inner tube 40 is open such that it may accommodate an endoscope to assist the physician in achieving the target site. With the catheter assembly 34 positioned properly at the target site, the forward safety catch release member 68 is depressed so that the member 68 may pass beneath the insertion stop 70c. The forward loop handle 66 is moved proximally from the forward position "B" toward the retracted position "A" until the member 68 encounters the pre-release stop 70b. Just prior to encountering the pre-release stop 70b, the member 68 passes under the obstruction 81, thus forcing the physician to remove his or her finger from the release member 68.

At this pre-release position, the physician is given the opportunity to ensure again that the stent 20 is in the proper position for release. FIG. 10 shows the approximate positions of the securing member 50 and the stent 20 at the pre-release position. However, the stent 20 shown in FIG. 10 is flared as it would be when following the guide 86 during a loading operation. During a delivery operation, such as is being described, the stent 20 does not exhibit flaring. The stent 20 is partially exposed and extending from the distal end of the tool 30.

Figure 12:
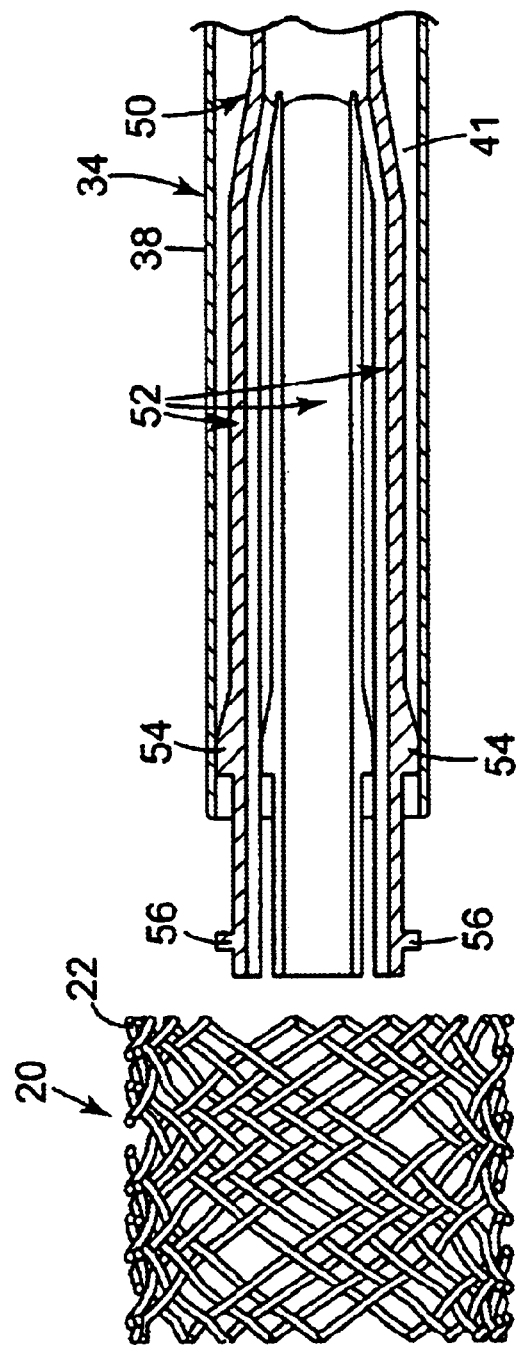
FIG. 12 is an enlarged cross-sectional elevation of a stent just deployed by a preferred delivery device of the present invention in the deployment position.

Satisfied with the positioning of the stent, the physician again depresses the catch release member 68 and pulls the forward loop handle 66 proximally toward the "A" position. However, the "A" position is not attainable because the member 68 abuts against the deployment stop 70a and the side surfaces of the loop handle simultaneously abut against the side catches 78. Thus, the forward loop handle 66 has reached the deployment position. FIG. 12 shows the relative positions of the outer tube 38, the inner tube 40, the securing member 50, and the stent 20 at the deployment position. The stent 20 is clear from the confines of the outer tube 38 and expands, freeing itself from the lugs 56 of the arms 52. The pads 54, however, are still confined within the outer tube 38, thereby preventing the arms 52 from spreading and preventing the lugs 56 from interfering with the deployment of the stent 20. The side catches 78 prevent further rearward movement of the second loop handle 66 toward position "A" regardless of whether the release member 68 is depressed. This prevents damage to tissue resulting from excessive spreading by the arms 52. With the stent 20 implanted at the desired location, the delivery tool 30 is then retracted leaving the stent 20 inside the body canal. The physician may choose to return the outer tube 38 to the pre-deployment position such that the lugs 56 are secure within the outer tube 38 prior to removing the device 30 from the patient.

Figure 13:
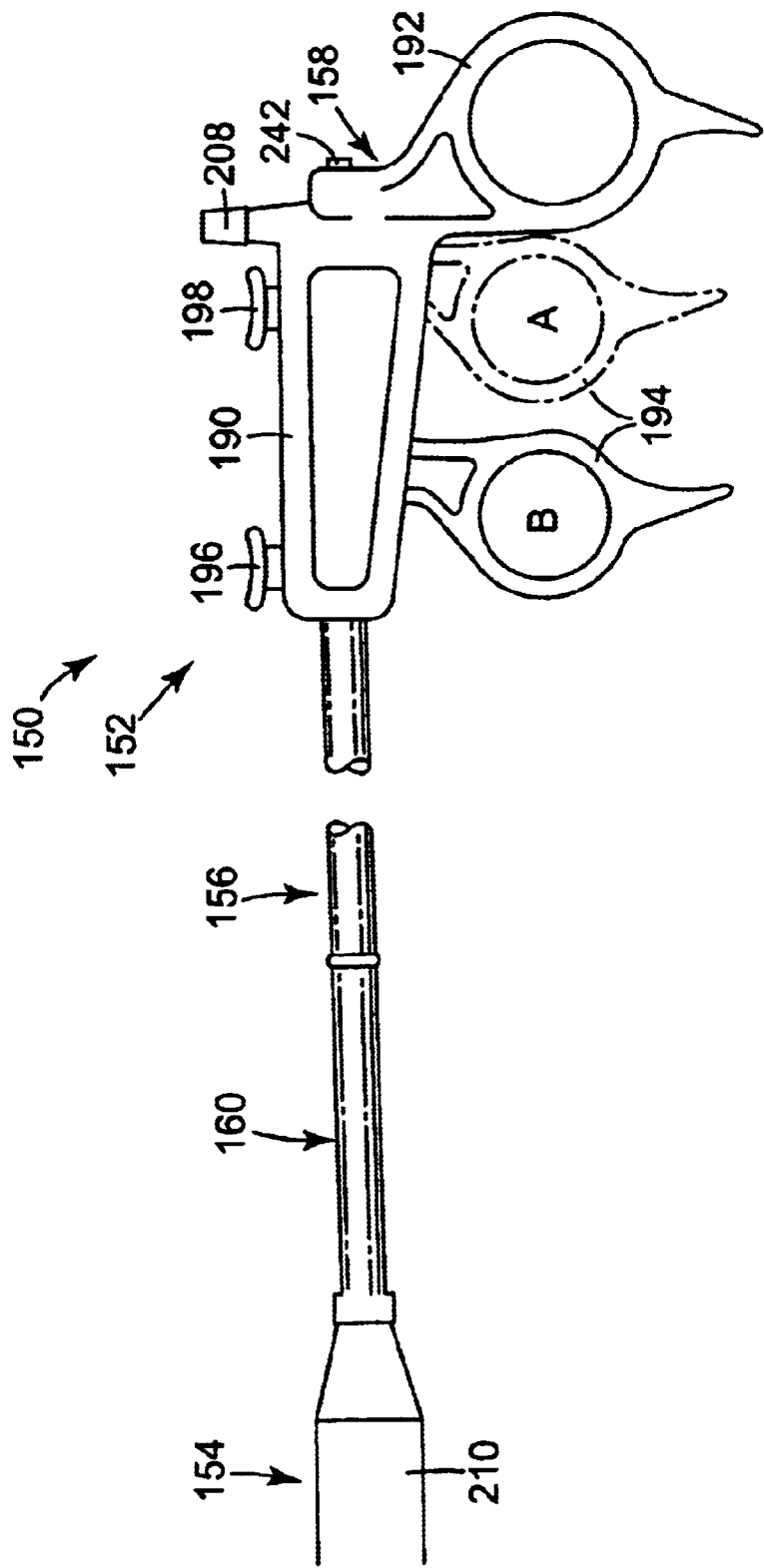
FIG. 13 is a side view of another examplary delivery system in accordance with the present invention for delivering a stent.
Figure 14:
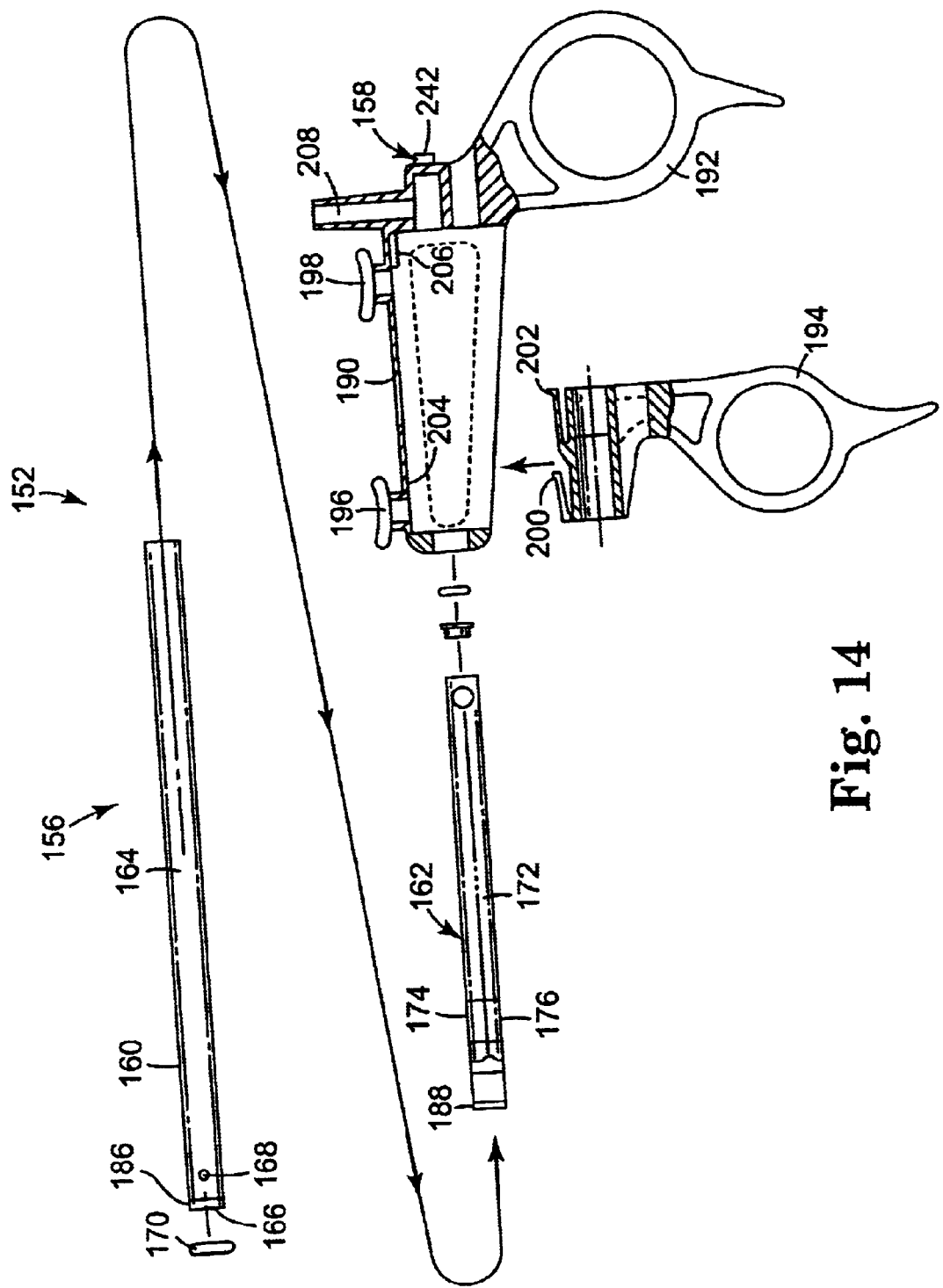
FIG. 14 is an exploded side view of a delivery tool for the delivery system of FIG. 9.

Referring to FIGS. 13 and 14, another embodiment of a delivery system 150 in accordance with the principles of the present invention is illustrated. The delivery system 150 includes a delivery tool 152 and a stent cartridge 154. The self-expanding stent 20 is stored in an expanded state in the stent cartridge 154. It is noted that the delivery system 150 may also be used to deliver non self-expanding prostheses such as a balloon expandable stent. The stent cartridge 154 is attached to the distal end of the delivery tool 152.

The delivery tool 152 includes a catheter assembly 156 and a hand piece 158. The catheter assembly 156 is about 25 cm in length and includes an outer tube 160 and an inner tube 162. The outer tube 160 has a lumen 164 extending from a proximal end to a distal end, and the distal end portion includes a distal port 166 and at least one side port 168 for the release of a contrast media or other solutions. The distal end is further-provided with a rounded collar 170 to facilitate insertion during implantation and to prevent trauma to the body canal.

The outer tube 160 should be strong enough to withstand the expansion force of the stent 20 but should also be flexible to allow intraluminal maneuvering. However, in applications where a flexible outer tube is not required, stainless steel or other rigid tubing may be used. The inner tube 162 is slidably received within the lumen 164 of the outer tube 160. The inner tube 162 includes a lumen 172 for the passage of a guide wire (not shown) or other devices. A first 174 and second aperture 176 are located near the distal portion of the inner tube 162, and each of the apertures 174, 176 has a contact surface 178, 180. A first set of lugs 182 extend radially outwardly from the inner tube 162 and are disposed circumferentially thereof at a region distal to the apertures 174, 176. Similarly, a second set of lugs 184 extend radially outwardly from the inner tube 162 and are disposed circumferentially thereof at a region proximal to the apertures 174, 176. In the exemplary embodiment, the lugs 182, 184 are located immediately adjacent to the apertures 174,176.

To facilitate proper placement of the catheter assembly 156, one or more marker elements 186, 188 may be located at a predetermined position on the outer tube 160 and inner tube 162, respectively. The marker elements 160, 162 may be a band of metal or radiopaque material attached to the periphery of the outer tube 160, whereby correct placement of the catheter assembly 156 prior to deployment of the stent 20 may be checked by fluoroscopy. Preferably, the distal end of the inner tube 162 includes a radiopaque element, thereby given an indication of the location of the distal end of the stent 20 during fluorscopically guided prostheses placement.

The hand piece 158 comprises a main body 190 and integral therewith a rear loop handle 192. A forward loop handle 194 is slidable between extreme positions within the main body 190 indicated by dashed lines and full lines in FIG. 13 illustrating a retracted position "A" and a forward position "B", respectively. The outer tube 160 is fixedly attached to the forward loop handle 194 and is thus axially moveable forward and backward between the extreme positions by sliding the forward loop handle 194. The hand piece 190 includes a front safety catch release member 196 and a rear safety catch release member 198 corresponding to the two extreme positions "B" and "A", respectively. The release members 196, 198 cooperate with spring elements 200, 202, respectively, provided on the upper side of the forward loop handle 194 as shown in FIG. 14. The spring elements 200, 202 cooperate with safety catches 204, 206 provided on the inside of the main body 190. By pressing the release members 196, 198, the spring elements 200, 202, respectively, can be released from their engagement with the respective safety catches 204, 206 so that the forward loop handle 194 can be axially displaced together with the associated outer tube 160. The main body 190 further includes a fluid inlet 208 at the distal end to allow introduction of a fluid into the delivery tool 158.

Figure 18:
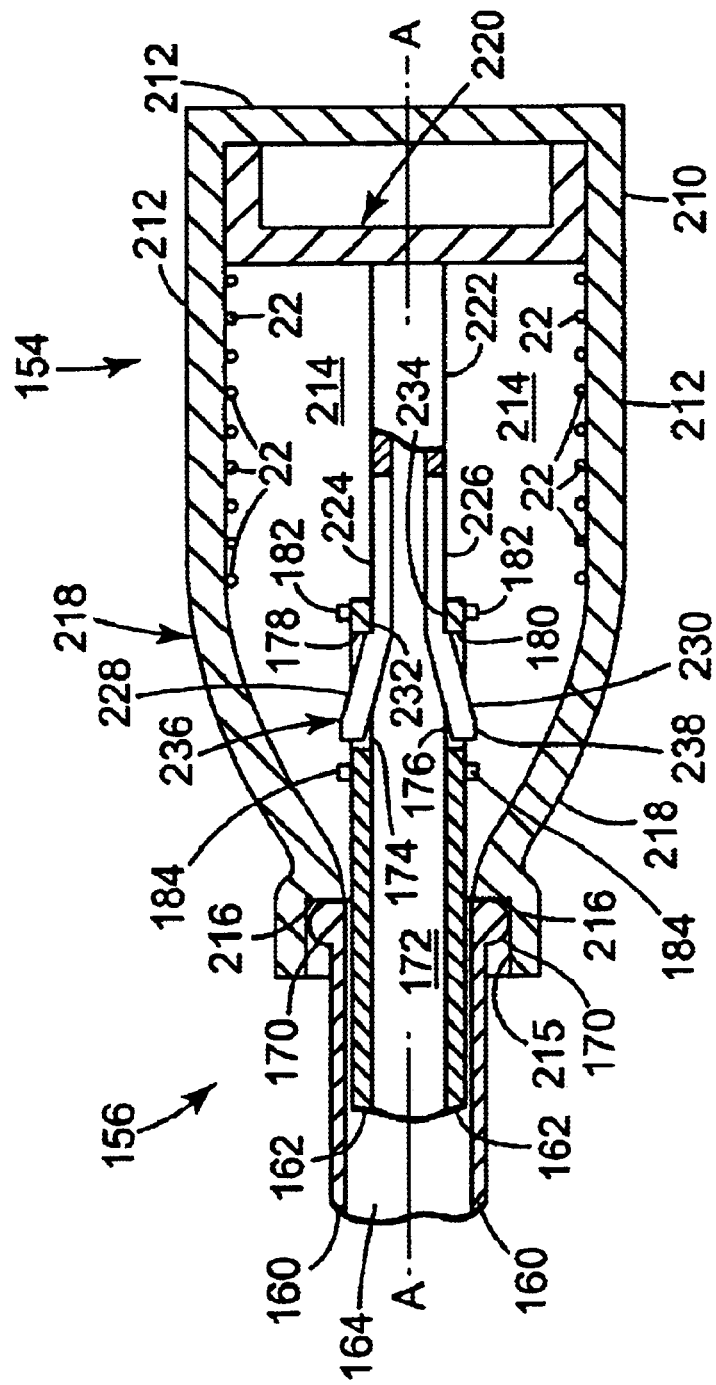
FIG. 18 is an enlarged cross-sectional view of the delivery system of FIG. 13 illustrating the stent stored within the stent cartridge.

Referring to FIG. 18, the stent cartridge 154 includes a casing 210 having walls 212 defining a chamber 214. The casing 210 has an opening 215 at a stent delivery end and is shaped and sized for slipping over the outer tube 160. A rest 216 within the stent delivery end is located for seating the casing 210 along an axis "A" and in position over the outer tube 160. A funnel portion 218 is located between the stent delivery end and the distal end of the stent cartridge 154. The funnel portion 218 is shaped for collapsing the self-expanding stent 20 before loading into the lumen 164 of the outer tube 160.

A piston 220 is located within the chamber 214, and the casing 210 is slideably moveable relative to the piston 220 from a retracted position to an extended position. The stent 20 is stored within the chamber 214 in an expanded state, wherein the stent 20 pushes against the inner surface of the casing wall 212. The distal end of the stent 20 abuts the proximal wall of the piston 220 such that the stent 20 remains axially fixed relative to the piston 220 and inner tube 162. The piston 220 is detachably coupled to the inner tube 162 by a shaft 222 having a distal end and a proximal end. The distal end of the shaft 222 is fixedly attached to the piston 220 while the proximal end portion of the shaft 222 includes a first 224 and second arm member 226 respectively having a first 228 and second latch 230 with contact surfaces 232, 234. When the piston 220 is coupled to the inner tube 162, the respective contact surfaces 232, 234 of the first 228 and second latch 230 are lockingly engaged with the contact surfaces 178, 180 of the first 174 and second aperture 176. Thus, the outer tube 160 and casing 210 are driven in the distal direction relative to the inner tube 162, shaft 222, piston 220 and stent 20 when the forward loop handle 194 is moved from the retracted position "A" to the forward position "B". The first 224 and second arm member 226 further include releasing surfaces 236, 238, respectively, which engage with the inner wall of the inner tube 162. As the outer tube 160 and casing 210 are moved distally, the releasing surfaces 236, 238 engage with the inner wall of the outer tube 160 and drive the arm members 224, 226 radially inwardly such that the shaft 212 and piston 220 are released from the inner tube 162. Before the shaft 212 and piston 220 disengage with the inner tube 162, the proximal portion of the stent 20 is collapsed as it passes the funnel portion 218 such that the stent 20 engages with the first 182 and second set of lugs 184. Thus, the stent 20 is securably engaged with the inner tube 162 as it enters the lumen 164 or stent capture zone 238 of the outer tube 160.

Figure 19:
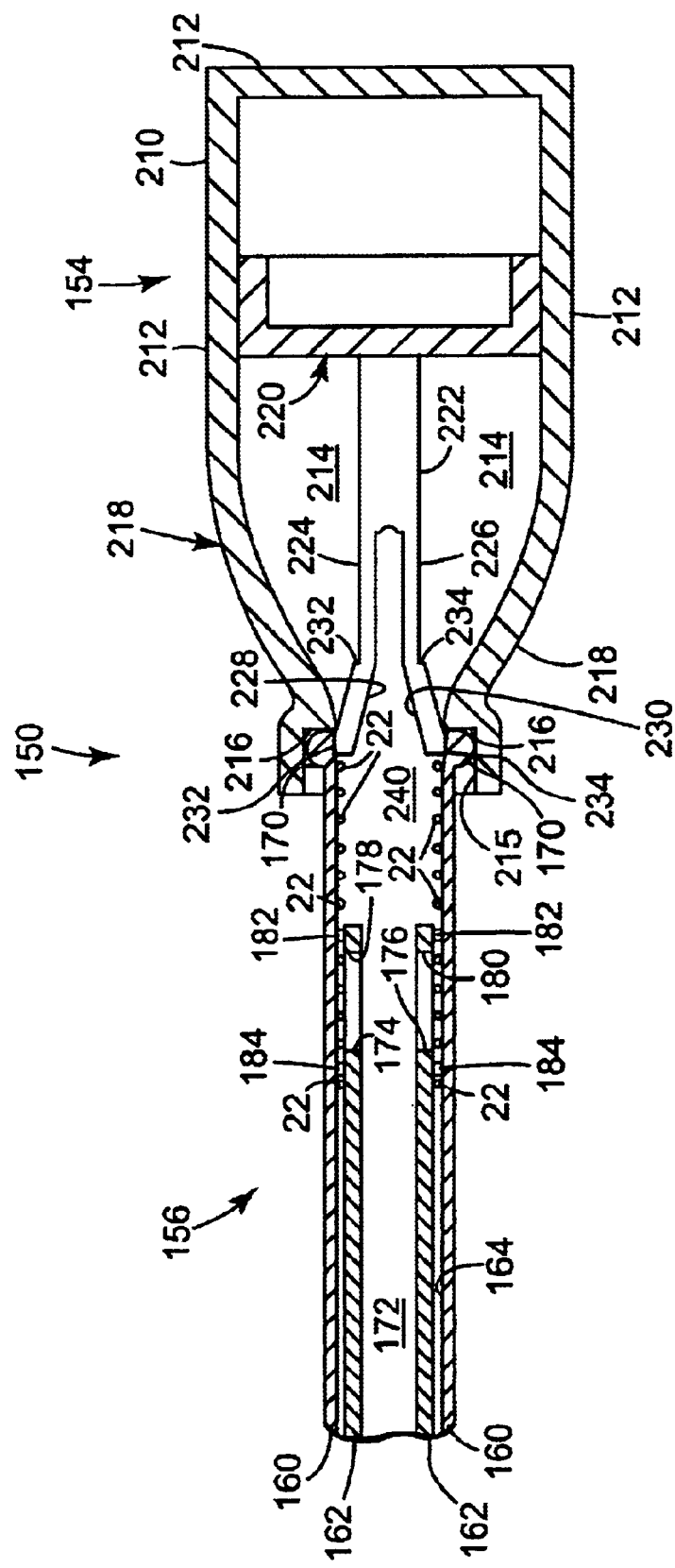
FIG. 19 is an enlarged cross-sectional view of the delivery system of FIG. 13 illustrating the stent transferred from the stent cartridge to the delivery tool.

Referring to FIG. 19, the lugs 182, 184 remain engaged with the wires 22 of the stent 20. The stent 20 may be released by depressing the front safety catch release member 196 and moving the forward loop handle 194 backward from the forward position "B" to the retracted position "A". The rear safety catch release member 198 arrests movement of the forward loop handle 194 before full release of the stent 20 as a safety measure to prevent an accidental release.

Figure 15:
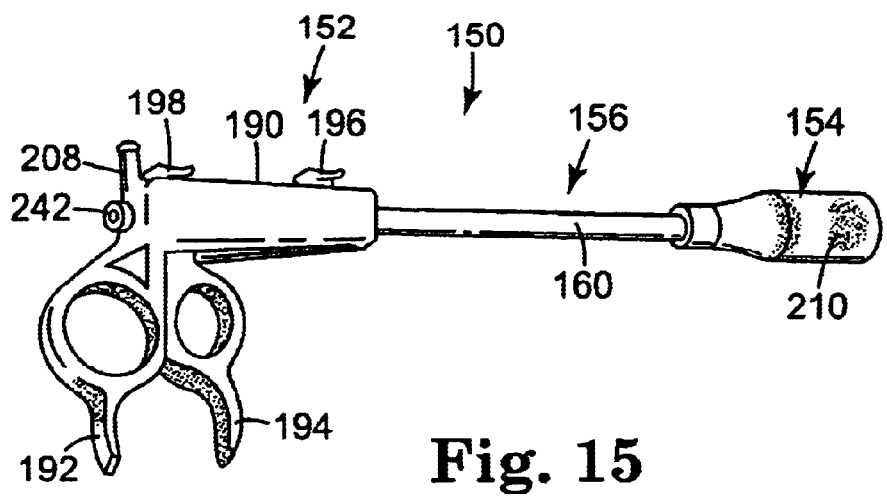
FIGS. 15–17 are perspective views of the delivery system of FIG. 13 illustrating the steps for loading and deploying a stent.
Figure 16:
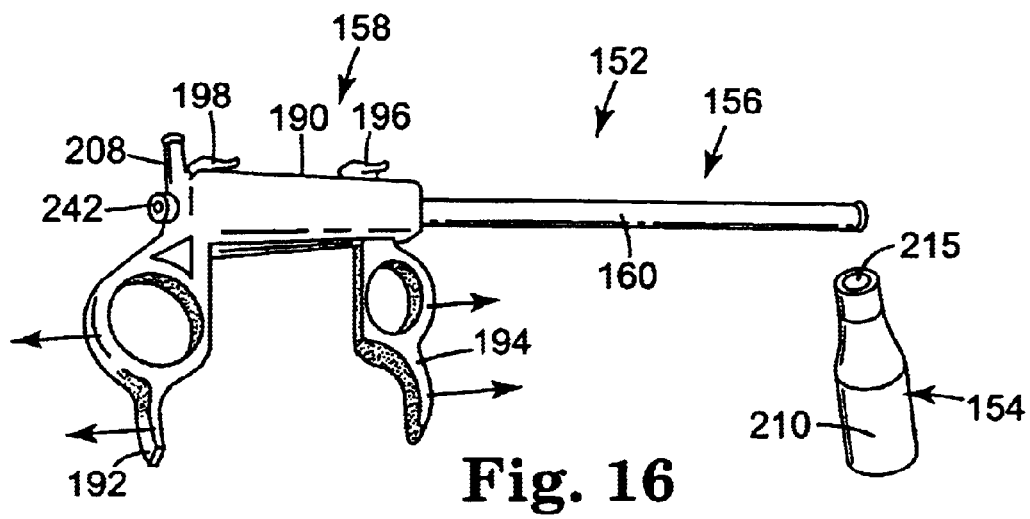

Operation of the delivery system 150 is as follows. As shown in FIGS. 15 and 18, the stent cartridge 154 is attached to the delivery tool 152 and may be provided in a sterile package. The forward loop handle 194 is in the retracted position "A", and the piston 220 and shaft 222 are secured to the inner tube 162 by having the contact surfaces 232, 234 of the first 228 and second latch 230 lockingly engaged with the contact surfaces 178, 180 of the first 174 and second aperture 176. Immediately prior to the implantation procedure, the stent 20 is transferred from the stent cartridge 154 to the delivery tool 152 by depressing the rear safety catch release member 198 and moving the forward loop handle 194 from the retracted position "A" to the forward position "B" as shown in FIGS. 16 and 19. When the forward loop handle 194 is moved to the forward position "B", the outer tube 160 and casing 210 are moved into the position shown in FIG. 19, and the front safety catch member 196 is activated to lock the forward loop handle 194. The outer tube 160 and casing 210 move distally while the inner tube 162, shaft 222, and piston 220 remain fixed relative to the main body 190. Movement of the stent 20 relative to the main body 190 is prevented because the distal end of the stent 20 abuts the distal surface of the piston 220. The funnel portion 218 of the casing 210 collapses the stent 20 and the wires 22 engage with the first 182 and second set of lugs 184 to lockingly secure the stent 20 to the inner tube 162, while the releasing surfaces 236, 238 engage with the inner wall of the outer tube 160 and disengage the contact surfaces 236, 238 of the first and second latch 228, 230 from the contact surfaces 178, 180 of the first 176 and second aperture 178 to release the piston 220 and shaft 222 from the inner tube 162. As the forward movement of the forward loop handle 194 is completed, the stent 20 is passed into the stent capture zone 240 of the outer tube 160 as shown in FIG. 19.

With the stent loaded in the delivery tool, the empty stent cartridge 154 is detached from the delivery tool as shown in FIG. 16. Assuming an introducer (not shown) has been inserted into the body canal, a guide wire (not shown) may be positioned at the occlusion site. The distal end of the catheter assembly 156 is passed over the guide wide via the lumen 172 of the inner tube 162 and directed to the occlusion site. In some applications, the catheter assembly 156 may be inserted into the body canal without an introducer, and a guide wire may then be passed through the proximal end of the lumen 172 of the inner tube via a port 242 and directed to the occlusion site. The catheter assembly 156 may then be directed to the desired location. In both procedures, the guide wire may be retained within the inner tube 162 until the stent 20 is deployed at the desired location and withdrawn together with the catheter assembly 156. Alternatively, the guide wire may be withdrawn prior to the deployment of the stent 20 so that correct positioning of the stent 20, while still within the catheter assembly 156, may be verified by endoscopic or fluoroscopic means or the like.

Figure 17:
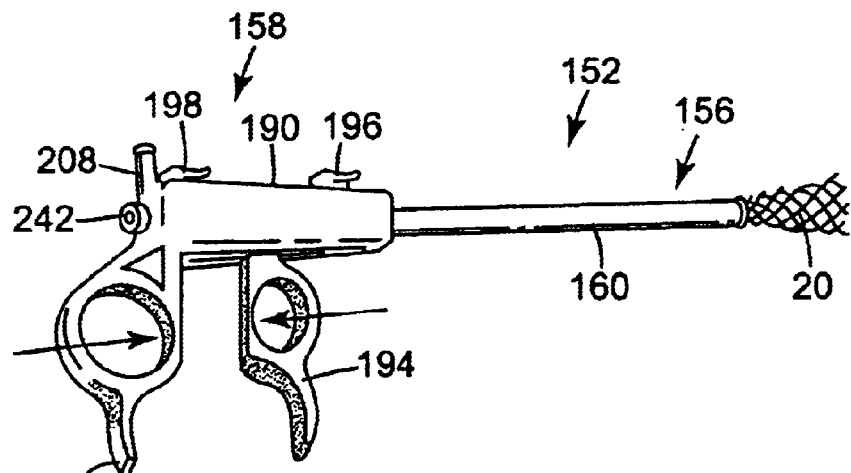
Figure 20:
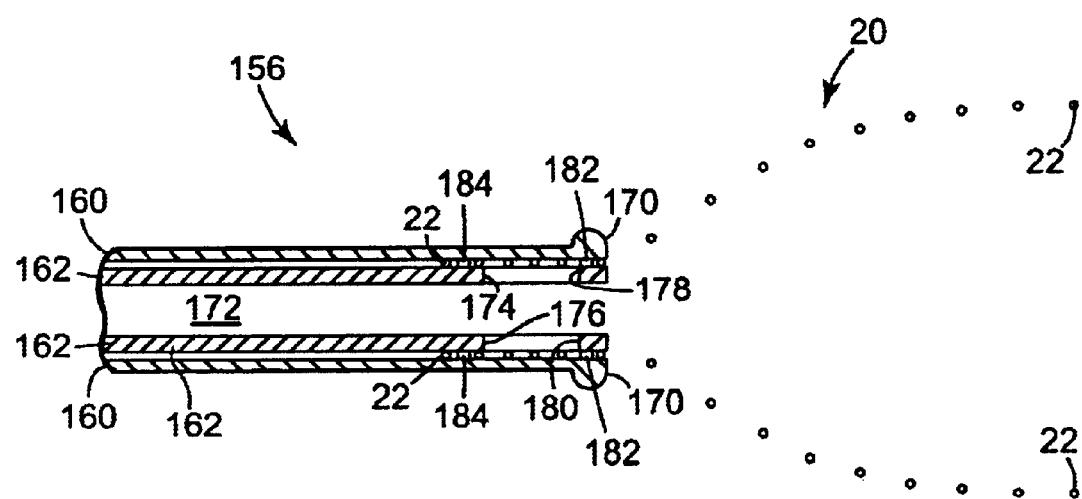
FIG. 20 is an enlarged cross-sectional view of the delivery system of FIG. 13 illustrating the stent being partially deployed.
Figure 21:
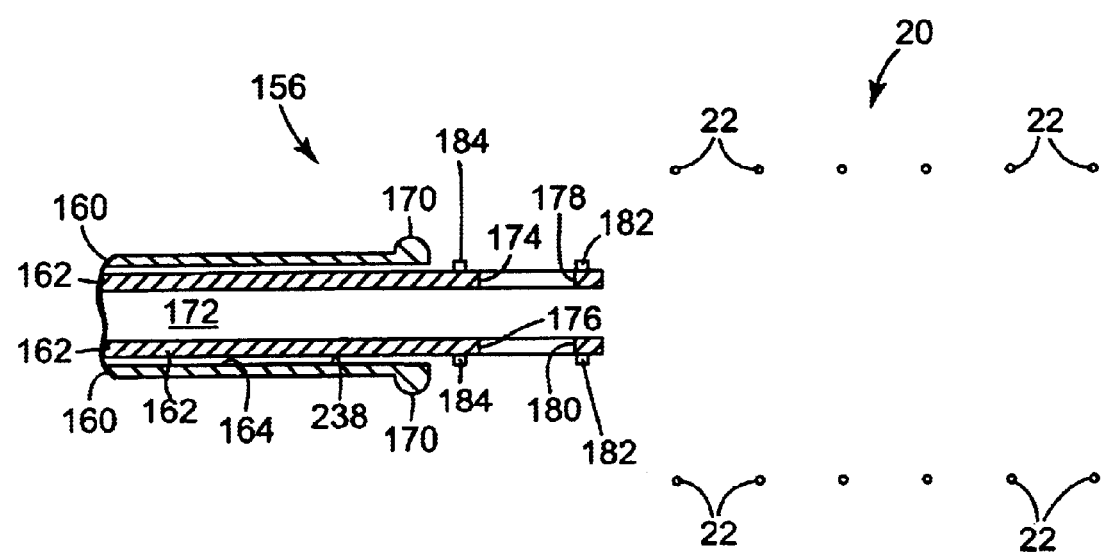
FIG. 21 is an enlarged cross-sectional view of the delivery system of FIG. 13 illustrating the stent being fully deployed.

With the catheter assembly 156 positioned properly, the forward safety catch release member 196 is activated by downward movement thereof, and the forward loop handle 194 is moved backward from the forward position "B" to the retracted position "A" to release the stent 20 as shown in FIGS. 17 and 20. As the forward loop handle 194 is moved backward, the outer tube 160 is retracted proximally such that the distal portion of the inner tube 162 and the stent 20 exit the lumen 164 of the outer tube 160. During the backward movement of the forward loop handle 194, the safety catch 206 arrests the movement before full release of the stent 20. Thus, movement of the outer tube 160 is limited to the extent that the lugs 182, 184 of the inner tube 162 remain within the lumen 164 of the outer tube 160 and the stent 20 remains lockingly secured to the delivery tool 152. Full release of the stent 20 is obtained by depressing the rear safety catch release member 198 and completing the backward movement of the forward loop handle 194, wherein the lugs 182, 184 exit the lumen 164 of the outer tube 160 and disengage with the stent 20 as shown in FIG. 21. With the stent implanted at the desired location, the delivery device is then retracted leaving the stent inside the body canal.

Although the present invention has been described in detail with regarding the exemplary embodiment and drawings thereof, it should be apparent to those skilled in the art that various adaptations may be accomplished without departing from the spirit and scope of the invention. For example, the stent does not have to be stored in the cartridge with its longitudinal axis coincident with the longitudinal axis of the catheter assembly. Furthermore, the stent may be stored in an expanded state in a braided tube which extends from the outer tube of the catheter assembly. During the loading procedure, the braided tube and stent may simultaneously pulled and compressed into the lumen of the outer tube. The braided tube may remain within the lumen during deployment of the stent, wherein a pusher tube within the lumen of the inner tube is used to push the stent through and out of the lumen of the outer tube. Further, other means may be utilized to drive the outer tube, or the outer tube may be fixed and the inner tube may be configured to move relative to the main body. Accordingly, the invention is not limited to the precise embodiments shown in the drawings and described in detail hereinabove.

What is claimed is:

1. A delivery system for intraluminal delivery of a self-expanding prosthesis at a site within a body canal, comprising:
    a housing sized and shaped to retain a self-expanding prosthesis in a first state;
    a delivery tool for manipulation by an operator and having a catheter assembly extending distally from the delivery tool and including a lumen with a capture zone, the capture zone sized and shaped to retain the self-expanding prosthesis in a compressed state that is radially smaller than the first state, the housing removably attached to the catheter assembly; and
    a securing mechanism movably disposed relative to the lumen and including a first portion slidable within the lumen and a second portion that is positionable within the housing to extend at least partially through the self-expanding prosthesis and including a radially extending feature to engage with the self-expanding prosthesis when in the first state thereof so that the securing mechanism and lumen can be moved relative to one another for transferring the self-expanding prosthesis from the housing to the capture zone.

2. The delivery system of claim 1, wherein the catheter assembly further comprises:
    an outer tube with the lumen;
    an inner tube with an inner lumen, the inner tube slideably received within the lumen of the outer tube and operably connected to the first portion of the securing mechanism; and, wherein the second portion of the securing mechanism comprises at least a portion of at least one flexible arm extending axially from a distal portion of the inner tube, the flexible arm having at least one lug engageable with the self-expanding prosthesis in the first state thereof, wherein the arm is radially movable between a first position to engage with the self-expanding prosthesis within the housing in the first state and a second position to be engaged with the prosthesis in the compressed state.

3. The delivery system of claim 2, wherein the housing further comprises:
a casing with a funnel portion; and
a guide with a funnel portion, the guide disposed within the casing to form a guide space therebetween, the flexible arm and self-expanding prosthesis being disposable within the guide space, and the self-expanding prosthesis being collapsible from an expanded first state to a compressed state when passing through the funnel portion.

4. The delivery system of claim 3, wherein the flexible arm and self-expanding prosthesis can pass through the guide space and into the capture zone when the outer tube is moved relative to the inner tube.

5. The delivery system of claim 4, wherein an outer surface of the lug can be positioned sufficiently proximate an inner wall of the outer tube when the flexible arm is in its second position such that the self-expanding prosthesis can be secured to the lug when in the capture zone.

6. The delivery system of claim 5, wherein the self-expanding prosthesis is releasable from the lug when the lug is outside the lumen of the outer tube.

7. The delivery system of claim 3, wherein the delivery tool further comprises a hand piece, the hand piece comprising:
a main body;
a rear loop handle disposed on the main body; and
a forward loop handle moveable between a retracted position and a forward position; and,
wherein the outer tube is fixed to the forward loop handle and thereby movable between the refracted position and the forward position.

8. The delivery system of claim 1, wherein the catheter assembly further comprises:
an outer tube with the lumen; and
an inner tube with an inner lumen, the inner tube slidably received within the lumen of the outer tube; and
the securing mechanism comprises:
a piston slidable for forming the second portion of the securing mechanism and positioned within a chamber of the housing, the piston being positionable so that a distal end of the self-expanding prosthesis can be abutted by a proximal face of the piston; and
a shaft including the first portion of the securing mechanism and having a proximal portion removably attached to the inner tube and a distal portion coupled to the piston.

9. The delivery system of claim 8, wherein the securing mechanism further comprises:
at least one aperture at a distal portion of the inner tube, the at least one aperture having a contact surface; and
lugs extending outwardly from the inner tube, the lugs engageable with the self-expanding prosthesis;
wherein the shaft has at least one arm member with a releasing surface and a contact surface;
wherein the shaft is secured to the inner tube when the contact surface of the shaft is engaged with the contact surface of the at least one aperture; and
wherein the shaft is released from the inner tube when outer tube is moved distally relative to the inner tube, wherein the releasing surface of the shaft engages an interior wall of the outer tube such that the contact surface of the shaft disengages with the contact surface of the at least one aperture, and wherein the self-expanding prosthesis can be collapsed from the expanded state to a compressed state when transferred from the chamber to the lumen of the outer tube.

10. The delivery system of claim 9, wherein the housing further comprises a funnel portion, the self-expanding prosthesis collapsible from an expanded state to a compressed state when passing through the funnel portion.

11. The delivery system of claim 9, wherein outer surfaces of the lugs can be positioned sufficiently proximate an inner wall of the inner tube such that the self-expanding prosthesis can be secured to the lugs when in the capture zone of the outer tube.

12. The delivery system of claim 11, wherein the self-expanding prosthesis is deployable from the delivery tool by moving the outer tube proximally relative to the inner tube such that the lugs exit the lumen of the outer tube and are thereby disengageable with the self-expanding prosthesis.

13. The delivery system of claim 8, further comprising:
wherein the delivery tool further comprises a hand piece, the hand piece comprising:
a main body;
a rear loop handle disposed on the main body; and
a forward loop handle moveable between a retracted position and a forward position;
wherein the outer tube is fixedly attached to the forward loop handle and moveable between the retracted position and the forward position.

14. The delivery system of claim 1, further comprising in combination a self-expanding prosthesis provided within the housing, wherein the self-expanding prosthesis is a self-expanding stent.

15. The delivery system of claim 14, wherein the self-expanding stent is metallic.

16. The delivery system of claim 14, wherein the self-expanding stent is polymeric.

17. The delivery system of claim 14 wherein the self-expanding stent is a braided stent.

18. The delivery system of claim 14 wherein the self-expanding stent is a fenestrated stent.

19. The delivery system of claim 1, wherein the housing is a cartridge.

20. A method for preparing an expandable prosthesis to be delivered within a body canal, the method comprising:
providing a delivery system having a housing removably attached to a delivery tool, the delivery tool including a catheter assembly with a lumen and a capture zone;
wherein the expandable prosthesis is stored in a first state within the housing; and
transferring the expandable prosthesis from the housing to the capture zone of delivery tool by engaging the expandable prosthesis with a radially extending feature of securing mechanism that is at least partially positioned through the expandable prosthesis and movably disposed relative to the lumen while the expandable prosthesis is in the first state and pulling the expandable prosthesis into the capture zone while also compressing the expandable prosthesis from the first state to a compressed state during the transfer.

21. The method of claim 20, wherein transferring the expandable prosthesis from the cartridge to the delivery tool further comprises:
moving an outer tube distally relative to an inner tube;
wherein the inner tube is disposed within the lumen provided through at least a portion of the outer tube, the inner tube having at least one flexible arm extending outwardly from the inner tube, the at least one flexible arm having at least one lug secured to the expandable prosthesis such that the expandable prosthesis passes from the housing into the capture zone of the lumen of the outer tube when the outer tube is moved distally relative to the inner tube.

22. The method of claim 21, wherein the expandable prosthesis is collapsed from the first state to the compressed state when passed through a funnel portion of the housing.

23. The method of claim 22, further comprising:
forming a guide space within the housing; and
passing the at least one flexible arm, at least one lug, and expandable stent through the guide space and into the lumen of the outer tube;
wherein the expandable prosthesis is collapsed from the first state to the compressed state when passing through the guide space adjacent the funnel portion, the guide space also moving the lug of the flexible arm radially from a first position within the housing to a second position to fit within the lumen.

24. The method of claim 23 wherein passing the at least one flexible arm, at least one lug, and expandable stent through the guide space and into the lumen of the outer tube comprises passing a plurality of flexible arms, each having one lug, and expandable stent through the guide space and into the lumen of the outer tube.

25. The method of claim 23, further comprising:
providing the delivery tool with a main body, a rear loop handle disposed on the main body, and a forward loop handle moveable between a retracted position and a forward position;
fixedly attaching the outer tube to the forward loop handle such that the outer tube is moveable between the retracted position and the forward position.

26. The method of claim 20, wherein transferring the expandable prosthesis from the housing to the delivery tool further comprises:
engaging the expandable prosthesis by a surface of a piston that is slidably disposed within the housing, the piston having a shaft with a release surface engageable with an inner wall of the outer tube, the shaft further having a contact surface;
securing the piston to an inner tube which is slideably disposed within the lumen of an outer tube, the inner tube having at least one aperture at a distal portion thereof, the at least one aperture having a contact surface engaged with the contact surface of the shaft, the inner tube having lugs extending radially outwardly, the lugs engageable with the expandable prosthesis; and,
releasing the piston and the shaft from the inner tube by sliding the outer tube distally relative to the inner tube such that the release surface engages the inner wall of the outer tube and disengages the contact surface of the shaft from the contact surface of the at least one aperture;
wherein the expandable prosthesis is secured to the inner tube when the lugs engage with the expandable prosthesis.

27. The method of claim 26, further comprising:
deploying the expandable prosthesis from the delivery tool by moving the outer tube proximally relative to the inner tube such that the lugs exit the lumen of the outer tube and disengage with the expandable prosthesis.

28. The method of claim 26, further comprising:
providing the delivery tool with a hand piece, the hand piece having a main body, a rear loop handle disposed the main body, and a forward loop handle moveable between a retracted position and a forward position; and
fixedly attaching the outer tube to the forward loop handle such that the outer tube is moveable between the retracted position and the forward position.

29. The method of claim 20, wherein the expandable prosthesis is a self-expanding stent.

30. The method of claim 29, wherein the self-expanding stent is metallic.

31. The method of claim 29, wherein the self-expanding stent is polymeric.

32. The method of claim 20, wherein the housing is a cartridge.

33. The method of claim 20, wherein the body canal is a urethra.

34. A delivery system for intraluminal delivery of a prosthesis at a site within a body canal, comprising:
a cartridge comprising:
a stent guide sized and shaped to fit within an interior of the prosthesis, thereby permitting a prosthesis to be retained in a substantially expanded state;
a housing for operably supporting the stent guide and having a receiving chamber being sized and shaped to substantially encase at least a portion of said guide and to provide a space between said guide and an inner surface of the housing to retain said prosthesis, said housing and guide also including tapered portions that define a further radially decreasing space that leads to a proximal opening of the housing, the radially decreasing space to direct and reshape said prosthesis when said prosthesis is moved toward the proximal opening in said housing; and
a securing member having a first portion at a proximal end and a second portion at a distal end, said second portion being removably attachable to the prosthesis and useable to move the prosthesis through said proximal opening in said housing; and
a delivery tool having a catheter assembly including a lumen with a capture zone, the capture zone sized and shaped to retain the expandable prosthesis in a compressed state, the delivery tool removably attachable to the cartridge and the first portion of the securing member being slidably disposable relative to and at least partially within the lumen.

35. The delivery system of claim 34, wherein said delivery tool further comprises an inner tube slideably disposed within the lumen of said catheter assembly, and having a distal end attachable to said securing member proximal end, said inner tube constructed and arranged such that when said inner tube is attached to said securing member, sliding said inner tube proximally relative to said catheter assembly causes said securing member to move the prosthesis into said capture zone.

36. The delivery system of claim 35 wherein said inner tube distal end and said securing member proximal end each comprise threads constructed and arranged to mate with each other.

37. The delivery system of claim 34 further comprising a cap attachable to said cartridge housing and useable to maintain a closed environment in said space when said cartridge is detached from said delivery tool.

38. A cartridge, attachable to a delivery device for intraluminal delivery of a self-expanding prosthesis at a site within a body canal, the cartridge useable to transfer the self-expanding prosthesis from within the cartridge to a capture zone within the delivery device, the cartridge comprising:

a housing sized and shaped to retain the self-expanding prosthesis in a first state, the housing also having a tapered portion leading to a proximal opening that is for connection to a capture zone of a lumen of the delivery device;

a self-expanding prosthesis provided within the housing in the first state, which is a substantially expanded state thereof, and a securing mechanism operably attached at a first portion thereof to the self-expanding prosthesis and attachable at a second portion thereof to the delivery device, the first portion of the securing mechanism at least partially extending within the substantially expanded prosthesis, and the second portion of the securing mechanism being connectable to the delivery device to pull the self-expanding prosthesis from the housing to the capture zone within the delivery device when the securing member is attached to the delivery device.

39. The cartridge of claim 38, wherein the securing mechanism has at least one flexible arm extending axially from the second portion, each of the at least one flexible arms having at least one lug engageable with the self-expanding prosthesis.

40. The cartridge of claim 39, wherein the housing further comprises:

a casing with a funnel portion; and a guide with a funnel portion, the guide disposed within the casing to form a guide space therebetween, the at least one flexible arm and self-expanding prosthesis disposed within the guide space, and the self-expanding prosthesis being collapsible from an expanded state to a compressed state when passing through the funnel portions.

41. The cartridge of claim 38 further comprising a cap constructed and arranged to cover an open end of the housing and removably attached thereto, the cap thereby protecting the prosthesis from contamination prior to transferring the prosthesis from the cartridge to the delivery device.

42. The cartridge of claim 41 wherein the cap is further constructed and arranged to form a gas tight seal over the open end of the housing such that the housing may be pressurized with a gas during storage.

43. The cartridge of claim 38 wherein the securing member second portion comprises threads attachable to mating threads formed on a tube of said delivery device.

* * * * *

UNITED STATES PATENT AND TRADEMARK OFFICE
CERTIFICATE OF CORRECTION

PATENT NO.         : 6,926,732 B2
APPLICATION NO.    : 09/962402
DATED              : August 9, 2005
INVENTOR(S)        : Patricia M. Derus, Stephen L. Bolea and John W. Westrum, Jr.

It is certified that error appears in the above-identified patent and that said Letters Patent is hereby corrected as shown below:

Column 5, Line 12: delete "2-5" and insert -- 2-4 --

Column 5, Lines 57-58: delete "defined by the body 68"

Column 6, Line 54: delete "5" and insert -- 5a --

Column 9, Line 38: delete "41" and insert -- 48 --

Column 9, Line 44: delete "41" and insert -- 48 --

Column 10, Line 14: delete "9-10" and insert -- 9 --

Column 11, Line 54: delete "160, 162" and insert -- 186, 188 --

Column 15, Claim 7, Line 42: delete "refracted" and insert -- retracted --

Signed and Sealed this

Second Day of October, 2007

JON W. DUDAS
*Director of the United States Patent and Trademark Office*